(12) United States Patent
Johnson et al.

(10) Patent No.: US 6,278,039 B1
(45) Date of Patent: Aug. 21, 2001

(54) *C. ELEGANS* DELETION MUTANTS

(75) Inventors: Carl Johnson, Black Earth, WI (US); Bethany Westlund, Brookline, MA (US); Dianne Parry, Pacifica, CA (US)

(73) Assignee: Axys Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/085,476

(22) Filed: May 27, 1998

Related U.S. Application Data

(60) Provisional application No. 60/047,993, filed on May 28, 1997.

(51) Int. Cl.[7] .................. A01K 67/00; A01K 67/033; C12N 15/00
(52) U.S. Cl. ............................. 800/8; 800/9; 800/12
(58) Field of Search ........................ 800/8, 9, 12

(56) References Cited

PUBLICATIONS

Rudel, et al., "Function and Regulation of GLP–1: An Evolutionary Approach," International Worm Meeting Abstract 517, HHMI and University of Wisconsin–Madison (1997).
Waterson, R., "The Sequence of C. elegans cosmid C18E3" Direct submission (submitted Apr. 18, 1997) by Genome Sequencing Center, St. Louis, MO.
Anderson, in *Caenorhabditis elegans: Modern Biological Analysis of an Organism*, eds. Epstein, H. F. and Shakes, D. C. (Academic Press, Inc. San Diego) 48:31–58 (1995).
Baumeister et al., *Genes and Function* 1:149–159 (1997).
Borchelt et al., *Neuron* 17:1005–1013 (1996).
Citron et al., *Nat. Med.* 3:67–72 (1997).
DeStrooper et al., *Nature* 391:387–390 (1998).
Duff et al., *Nature* 383:710–713 (1996).
Greenwald et al., *Cell* 34:435–444 (1983).
Hardy, *Trends Neurosci.* 20:154–159 (1997).
Jansen et al., *Nat. Genet.* 17:119–121 (1997).
Lambie and Kimble, *Development* 112:231–240 (1991).
Levitan and Greenwald, *Nature* 377:351–354 (1995).
Levitan et al., *Proc. Natl. Acad. Sci. USA* 93:14940–14944 (1996).
Li & Greenwald, *Proc. Natl. Acad. Sci.* 94:12204–12209 (1997).
L'Hernault and Arduengo, *J. Cell Biol.* 119:55–68 (1992).
Mello et al., *Cell* 77:95–106 (1994).
Moulder et al., Worm Meeting 1997 p. 3 (1997).
Moulder, Worm Meeting 1997, p. 342 (1997).
Naito et al., *Nuc. Acids. Res.* 20:2967–2969 (1992).
Plasterk, in *Caenorhabiditis elegans: Modern Biological Analysis of an Organism,* eds. Epstein, H. F. and Shakes, D. C. (Academic Press, Inc. San Diego) 48:59–80 (1995).
Plasterk, Worm Meeting 1997, p. 302 (1997).
Scheuner et al., *Nat. Med.* 2:864–870 (1996).
Shen et al., *Cell* 89:629–639 (1997).
Tomita et al., *Proc. Natl. Acad. Sci. USA* 94:2025–2030 (1997).
Westlund, Worm Meeting 1997 p. 171 (1997).
Wong et al., *Nature* 387:288–292 (1997).
Yandell et al., *Proc. Natl. Acad. Sci. USA* 91:1381–1385 (1994).

*Primary Examiner*—Deborah J. R. Clark
*Assistant Examiner*—Anne-Marie Baker
(74) *Attorney, Agent, or Firm*—Clark & Elbing LLP; Kristina Bieker-Brady

(57) ABSTRACT

Provided are worms having deletions in genes associated with Alzheimer's disease and methods for detecting genes and compounds involved in the causation of Alzheimer's disease or useful for the treatment of Alzheimer's disease. A novel method for constructing deletions in the nematode is also provided.

1 Claim, 14 Drawing Sheets

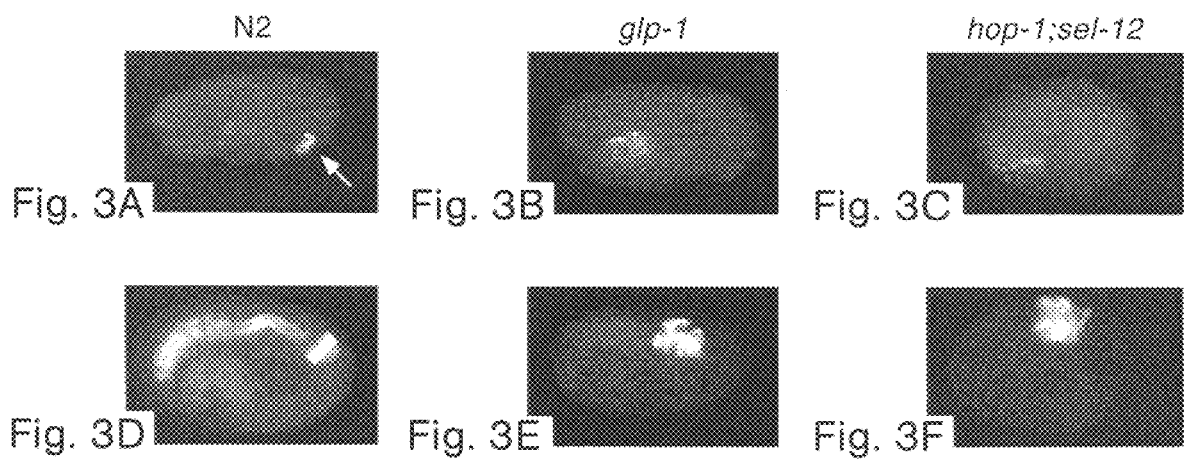

Seq ID NO:1 *sel-12(+)* bp 2525-2545 TCTATCAA T ATTTCTTTGGAA

Seq ID NO:2 *sel-12(+)* bp 3955-3975 CATA T TTTTTTTAACAATAAT

Seq ID NO:3 *sel-12(nr2011)* bp 2525-2545 TCTATCAATTTTTTTTAACAA

Fig. 8 hop-1(+) bp 2300-2320 AAACCAC A CACTTTCTAGACA hop-1(+) bp 3490-3510 GCTACACAATAAA A GCCCAAA hop-1(nr2003) bp 2300-2320 AAACCACAGCCCAAAATATAA

Fig. 10

FAD presenilin mutations are:

| | Loss of function | Gain of function |
|---|---|---|
| Relevant Suppressor Mutations | Loss-of-function (LOF) | Gain-of-function (GOF) |
| Relevant Revertants of LOF Suppressors | GOF | LOF |
| Relevant Revertants of GOF Suppressors | LOF | GOF |
| Relevant Phenocopy Mutations | GOF | LOF |

Fig. 13

SEQUENCE LISTING

<160> NUMBER OF SEQ ID NOS: 24

<210> SEQ ID NO 1
<211> LENGTH: 21
<212> TYPE: DNA
<213> ORGANISM: Caenorhabditis elegans

<400> SEQUENCE: 1
tctatcaata tttctttgga a                                              21

<210> SEQ ID NO 2
<211> LENGTH: 20
<212> TYPE: DNA
<213> ORGANISM: Caenorhabditis elegans

<400> SEQUENCE: 2
catatttttt taacaataat                                                20

<210> SEQ ID NO 3
<211> LENGTH: 21
<212> TYPE: DNA
<213> ORGANISM: Caenorhabditis elegans

<400> SEQUENCE: 3
tctatcaatt tttttaaca a                                               21

<210> SEQ ID NO 4
<211> LENGTH: 21
<212> TYPE: DNA
<213> ORGANISM: Caenorhabditis elegans

<400> SEQUENCE: 4
aaaccacaca ctttctagac a                                              21

<210> SEQ ID NO 5
<211> LENGTH: 21
<212> TYPE: DNA
<213> ORGANISM: Caenorhabditis elegans

<400> SEQUENCE: 5
gctacacaat aaaagcccaa a                                              21

<210> SEQ ID NO 6
<211> LENGTH: 21
<212> TYPE: DNA
<213> ORGANISM: Caenorhabditis elegans

<400> SEQUENCE: 6
aaaccacagc ccaaaatata a                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic primer based on Caenorhabditis
      elegans

<400> SEQUENCE: 7
catgttccat actggcaatc t                                              21

<210> SEQ ID NO 8

```
<211> LENGTH: 21
<212> TYPE: DNA
<213> ORGANISM: Artificial Sequence
<220> FEATURE:
<223> OTHER INFORMATION: Synthetic primer based on Caenorhabditis
      elegans

<400> SEQUENCE: 8
tccaggttta ctccagtctt g                                              21

<210> SEQ ID NO 9
<211> LENGTH: 19
<212> TYPE: DNA
<213> ORGANISM: Artificial Sequence
<220> FEATURE:
<223> OTHER INFORMATION: Synthetic primer based on Caenorhabditis
      elegans

<400> SEQUENCE: 9
gctcagggtt gacacactt                                                 19

<210> SEQ ID NO 10
<211> LENGTH: 21
<212> TYPE: DNA
<213> ORGANISM: Artificial Sequence
<220> FEATURE:
<223> OTHER INFORMATION: Synthetic primer based on Caenorhabditis
      elegans

<400> SEQUENCE: 10
ttacctttat tattggacga a                                              21

<210> SEQ ID NO 11
<211> LENGTH: 25
<212> TYPE: DNA
<213> ORGANISM: Artificial Sequence
<220> FEATURE:
<223> OTHER INFORMATION: Synthetic primer based on Caenorhabditis
      elegans

<400> SEQUENCE: 11
tcaaagaccg ataatgttag ttgta                                          25

<210> SEQ ID NO 12
<211> LENGTH: 23
<212> TYPE: DNA
<213> ORGANISM: Artificial Sequence
<220> FEATURE:
<223> OTHER INFORMATION: Synthetic primer based on Caenorhabditis
      elegans

<400> SEQUENCE: 12
ttccagatat gccaactgaa gtg                                            23

<210> SEQ ID NO 13
<211> LENGTH: 23
<212> TYPE: DNA
<213> ORGANISM: Artificial Sequence
<220> FEATURE:
<223> OTHER INFORMATION: Synthetic primer based on Caenorhabditis
      elegans

<400> SEQUENCE: 13
gccgacctga aagataatga aat                                            23

<210> SEQ ID NO 14
<211> LENGTH: 22
```

```
<212> TYPE: DNA
<213> ORGANISM: Artificial Sequence
<220> FEATURE:
<223> OTHER INFORMATION: Synthetic primer based on Caenorhabditis
      elegans

<400> SEQUENCE: 14
ataaagccga aggttagacg at                                              22

<210> SEQ ID NO 15
<211> LENGTH: 23
<212> TYPE: DNA
<213> ORGANISM: Artificial Sequence
<220> FEATURE:
<223> OTHER INFORMATION: Synthetic primer based on Caenorhabditis
      elegans

<400> SEQUENCE: 15
ttgtttgaaa ataggtggtt tgg                                             23

<210> SEQ ID NO 16
<211> LENGTH: 21
<212> TYPE: DNA
<213> ORGANISM: Artificial Sequence
<220> FEATURE:
<223> OTHER INFORMATION: Synthetic primer based on Caenorhabditis
      elegans

<400> SEQUENCE: 16
tctgtctggg aatcactgga g                                               21

<210> SEQ ID NO 17
<211> LENGTH: 22
<212> TYPE: DNA
<213> ORGANISM: Artificial Sequence
<220> FEATURE:
<223> OTHER INFORMATION: Synthetic primer based on Caenorhabditis
      elegans

<400> SEQUENCE: 17
gcagcaaaaa aggtcacatc cc                                              22

<210> SEQ ID NO 18
<211> LENGTH: 24
<212> TYPE: DNA
<213> ORGANISM: Artificial Sequence
<220> FEATURE:
<223> OTHER INFORMATION: Synthetic primer based on Caenorhabditis
      elegans

<400> SEQUENCE: 18
gtatggcatg acagatttcc acag                                            24

<210> SEQ ID NO 19
<211> LENGTH: 22
<212> TYPE: DNA
<213> ORGANISM: Artificial Sequence
<220> FEATURE:
<223> OTHER INFORMATION: Synthetic primer based on Caenorhabditis
      elegans

<400> SEQUENCE: 19
atcccctctc ttcgctgcta tc                                              22

<210> SEQ ID NO 20
<211> LENGTH: 24
<212> TYPE: DNA
```

```
<213> ORGANISM: Artificial Sequence
<220> FEATURE:
<223> OTHER INFORMATION: Synthetic primer based on Caenorhabditis
      elegans

<400> SEQUENCE: 20
caggaaagga atggaaatta gccc                                          24

<210> SEQ ID NO 21
<211> LENGTH: 23
<212> TYPE: DNA
<213> ORGANISM: Artificial Sequence
<220> FEATURE:
<223> OTHER INFORMATION: Synthetic primer based on Caenorhabditis
      elegans

<400> SEQUENCE: 21
ccgctcaagt tttgtctgca atc                                           23

<210> SEQ ID NO 22
<211> LENGTH: 23
<212> TYPE: DNA
<213> ORGANISM: Artificial Sequence
<220> FEATURE:
<223> OTHER INFORMATION: Synthetic primer based on Caenorhabditis
      elegans

<400> SEQUENCE: 22
cgccagcatt atcacactct gtg                                           23

<210> SEQ ID NO 23
<211> LENGTH: 23
<212> TYPE: DNA
<213> ORGANISM: Artificial Sequence
<220> FEATURE:
<223> OTHER INFORMATION: Synthetic primer based on Caenorhabditis
      elegans

<400> SEQUENCE: 23 cactagggt gtttgttttt ccc                                            23

<210> SEQ ID NO 24
<211> LENGTH: 22
<212> TYPE: DNA
<213> ORGANISM: Artificial Sequence
<220> FEATURE:
<223> OTHER INFORMATION: Synthetic primer based on Caenorhabditis
      elegans

<400> SEQUENCE: 24
agaaaggcga tgttgtgagg gc                                            22
```

C. ELEGANS DELETION MUTANTS

CROSS REFERENCE TO RELATED APPLICATIONS

This application claims priority from U.S. provisional application Ser. No. 60/047,993, filed May 28, 1997.

BACKGROUND OF THE INVENTION

The field of the invention is Alzheimer's disease.

Alzheimer's disease (AD) is a progressive neurodegenerative disorder of the central nervous system involving loss of memory and cognitive function. Neuropathological hallmarks of AD extracellular amyloid plaques, whose major component is the Aβ peptide, a proteolytic product of the β-amyloid precursor protein (APP).

Dominant mutations in any of three mammalian genes, PS1, PS2, and APP are causative for the early-onset, familial form of AD (FAD). PS1 and PS2 encode related proteins-, while APP encodes the amyloid precursor protein (APP) (reviewed in Hardy, Trends Neurosci. 20:154–159, 1997), from which the Aβ peptide is generated by proteolytic processing.

Since presenilin-1 (PS1) and presenilin-2 (PS2) were first identified as genes mutated in FAD, much effort has been devoted to elucidating the biological function of presenilins in normal and disease states. Two lines of evidence support a hypothesis that presenilins affect proteolytic processing of APP First, PS(FAD) mutations are associated with an increase in a longer, more amyloidogenic form of Aβ known as Aβ42; and second, levels of Aβ are decreased severalfold in neurons derived from PS1 knockout mice relative to PS1(+) control mice. Moreover, in neurons, Aβ 42 may be generated in the endoplasmic reticulum, where presenilins have been localized.

C. elegans has three presenilin genes, spe-4 (spermatogenesis defective) (L'Hernault, et al., J. Cell Biol., 119:55–68, 1992), sel-12 (suppressor and/or enhancer of lin-12) (Levitan et al., Nature 377:351–354, 1995), and hop-1 (homolog of presenilin) (Li et al., Proc. Natl. Acad. Sci USA 94:12204–12209, 1997). Rescue experiments using transgenes have shown that human PS1 and PS2 can substitute for SEL-12, demonstrating that presenilin function has been conserved from nematodes to mammals.

Construction of a nematode having mutations in nematode presenilin genes and also having phenotypes useful for screens for genes associated with the biological pathway and for screens for compounds affecting the biological pathway in which these genes function would be useful for identifying therapeutics and causative agents involved in AD.

SUMMARY OF THE INVENTION

We have discovered an improved nematode model for studying Alzheimer's disease and for screening for Alzheimer's therapeutics. Also provided is a novel method for reverse genetics.

In a first aspect, the invention features an isolated nucleic acid encoding a HOP-1 polypeptide having a mutation (preferably a deletion in or including the hop-1 gene), relative to a Hop-1 encoded by the wild-type hop-1 gene. In preferred embodiments the nucleic acid is cDNA, genomic DNA, or RNA and the mutation is a deletion.

In a third aspect, the invention features a nematode having an engineered mutation in the hop-1 gene, preferably a deletion. More preferably, the hop-1 nematode further includes a deletion or other null mutation in sel-12 or a deletion in spe-4. More preferably, the nematode has deletions or other null mutations in hop-1, sel-12, and spe-4. In a preferred embodiment, the nematode is homozygous for at least one of the aforementioned mutations.

In a fourth aspect, the invention features a method for identifying a compound capable of ameliorating diseases, including Alzheimer's disease. The method includes exposing a nematode having a hop-1 deletion or other mutation and a second deletion or other mutations in a gene selected from the group consisting of sel-12 and spe-4 to an effective amount of a compound and screening for an alteration in the phenotype of said nematode. Examples of such alterations are described herein below. An alteration in the phenotype of the nematode indicates a compound capable of ameliorating disease. Preferably, the phenotype is a phenotype conferred by the presence of hop-1, sel-12, spe-4, or the combination thereof, present in the nematode being used in the screen. In a preferred embodiment of this method the second mutation is a mutation in sel-12, the phenotype is selected from the group consisting of dead eggs or sterility, and the alteration is an alteration in either the number viable eggs or fertile offspring where such eggs or offspring, would otherwise be absent. Additional phenotypes which may be screened for to detect compounds which positively or negatively affect the genesis and progression of AD are also a part of the invention. Such screens identify both potential prophylactics and therapeutics for AD and environmental agents which may exacerbate the disease. In some of these embodiments of the invention wild-type worms or single mutations may be used (see the Detailed Description, below).

In a fifth aspect, the invention provides a method for identifying a gene involved in the development or amelioration of disease, e.g., Alzheimer's disease. The method includes selecting or screening for a reversion mutation (suppressor mutation) in a nematode having a hop-1 deletion and at least one additional second mutation in a gene selected from the group consisting of sel-12 and spe-4, and screening for an alteration in the phenotype of said nematode, an alteration in the phenotype of said nematode indicating a compound capable of ameliorating the disease. In preferred embodiments the second deletion is a deletion in sel-12 or sel-12 and spe-4, the phenotype is selected from the group consisting of dead eggs or sterility and those phenotypes provided herein, and the alteration is an alteration either of viable eggs or fertile offspring where such eggs or offspring, would otherwise be absent or one of the additional alterations provided herein. In a preferred embodiment, the method includes the additional step of screening for suppressors of the suppressor genes identified in the first selection or screen. In this embodiment, the suppressor gene is preferably placed in a genetic background in which it has a discernable phenotype.

In a related aspect, the invention provides a method for screening for genes associated with AD wherein the starting strains lack mutations in spe-4, hop-1, or sel-12. In this aspect the method includes looking for those phenotypes identified herein to be associated with the hop-1; spe-4 and hop-1; sel-12 worms or the hop-1; spe-4; sel-12 triple mutant.

In the seventh aspect, the invention features a method for constructing a nematode having a genetic deletion in a region of choice. The method includes the steps of: a) exposing said nematode to an appropriate mutagen; b) propagating said nematode for at least one generation; c) amplifying the nucleic acids of said nematode using at least two nucleic acid primers from the region of choice in the genome; and d) detecting the presence of a amplified nucleic acid which is shorter than the amplified nucleic acid from a non-mutagenized nematode. In preferred embodiments, the mutagen is selected from the group consisting of ethyl methanesulfonate, nitrosoguanidine, diethyl sulfate, N-nitroso-N-ethylurea, acetaldehyde, diepoxyoctane, diepoxybutane, trimethylpsoralen followed by UV irradiation, $^{32}$P decay, and ionizing particles. In another embodiment the mutagen is γ-irradation, ultraviolet irradiation, or X-irradiation.

In various other preferred embodiments the nematode is *C. elegans*; the method further comprises the steps of initially amplifying nucleic acid from a pool of nematodes said pool comprising at least 1000 genomes derived from distinct mutagenized nematodes; the primers have the sequences of nucleic acids within 10 kilobases of said region of choice (more preferably within 5 kilobases of said region); the nematode exposed to said mutagen is a part of a pool of at least 1000 nematodes; the detecting includes at least two rounds of amplifying, the first round of said amplifying being amplifying of nucleic acid using nucleic acid isolated from a pool of nematodes, said pool including at least 1000 nematodes genomes from the original mutagenesis.

In another preferred embodiment, the nematode being mutagenized has a genetic marker within 5 map units of the nucleic acids where said genetic alteration is desirable or, even more preferably has a second genetic markers within 5 map units of the first genetic marker, the second genetic marker being on the opposite side of the nucleic acids in the region of choice, relative to the first genetic marker. Where genetic markers are used they may be dominant or recessive.

Preferred primers have sequences which are within 5 kilobases of each other in a non-mutagenized nematode genome.

By "deletion" is meant removal of at least 1 nucleotide from the target region of the genome. Preferably, the number of nucleotides removed is between 200 and 5000 and, most preferably, between 500 and 3000. Most preferably, the deletion is sufficient to reduce or eliminate a biological function of a protein encoded by the nucleic acid region of choice. "Deletion" as used herein in the context limited to hop-1, spe-4, and sel-12 may also include null mutations other than deletions. Preferably, such null mutations have a low frequency of reversion.

By "nematode" is meant any nematode of the class Secernentea useful for genetic research. For example, *C. elegans*, *C. briggsae*, and *C. vulgaris* may be used. Most preferably, the nematode is *C. elegans*.

By "region of choice" is meant any nucleic acid region in the nematode where a deletion is desired. For example, a nucleic acid region that is capable encoding for a polypeptide sequence, capable of regulating gene expression, capable of regulating RNA stability, or capable of altering chromosome structure are all included.

By "Bag of Dead Eggs" means a phenotype which is the phenotype observed in hop-1;sel-12 and hop-1/sel-12/+ progeny animals segregating from a hop-1/+;sel-12/+ or hop-1/+; sel-12. The phenotypes include homozygotes that have a combined maternal-effect embryonic lethality and Egl phenotype.

BRIEF DESCRIPTION OF THE DRAWING

FIG. 2A) A gonad arm of a young adult hermaphrodite containing undifferentiated germ cells (gc) near the distal tip cell (dtc) and oocytes (ooc) and sperm (sp) proximally. FIG. 2B) A Glp-1-like (Austin et al., Cell 51:589–599, 1987) gonad arm containing sperm (sp) distally as well as proximally, but no oocytes or undifferentiated germ cells. This field of view also shows a protruding vulva (Ppvul). FIG. 2C) An L4 hermaphrodite containing a single anchor cell (AC). FIG. 2D) An L4 hermaphrodite containing two Acs. Scale bars, 10 μm.

FIGS. 3A–3F show strain B hop-1;sel-12 embryos exhibit defects similar to those observed in a conditional glp-1(lf) mutant. (FIGS. 3A–3C) Immunofluorescence micrographs of embryos stained with the monoclonal antibody J126 in order to visualize the intestinal valve cells (Mango et al., Development 120:2305–2315 1994). FIG. 3A The arrow points to a pair of intenstinal valve cells in a wild-type embryo. Neither glp-1 (Mello et al., Cell 77:95–106 1994) FIG. 3B nor hop-1;sel-12 FIG. 3C mutant embryos exhibit intestinal valve cell staining. The embryo in the FIG. 3C mutant embryos exhibit intestinal valve cell staining. The embryo in FIG. 3C is representative os 25 embryos scored. Pharyngeal gland cells also stain with the J126 antibody (Mango et al., Development 120:2305–2315, 1994). Pharyngeal gland cell staining is visible in (FIGS. 3A–3C); in FIG. 3A most of the staining is in a different focal plane than that shown. FIGS. 3D–3F show immunofluorescence micrographs of embryof stained with the monoclonal antibody 9.2.1, which recognizes pharyngeal myosin C (Epstein et al., in Muscle Development, eds. Pearson & Epstein, Cold Spring Harbor Lab., Cold Spring Harbor, NY pp. 7–14, 1982). glp-1 (Priess et al., Cell 51:601–611 1987) (FIG. 3E) and hop-1;sel-12 (FIG. 3F) embryos have less pharyngeal tissue than a wild-type embryo (FIG. 3D). The embryo depicted in (FIG. 3F) is representative of more than 50 embryos scored. *C. elegans* embryos are approximately 50 μm in length.

FIG. 8 shows the location of the nr2011 deletion breakpoints. Relevant sequences from wild-type sel-12 and sel-12(nr2011) genomic DNAs are shown. Arrows point to possible deletion breakpoints. The nr2011 deletion was formed either by breakage of wild-type sel-12 sequences after bp 2532 and bp 3958 or after bp 2534 and bp 3959.

FIG. 10 shows the location of the nr2003 deletion breakpoints. Relevant sequences from wild-type hop-1 and hop-1 (nr2003) genomic regions are shown. Arrows point to possible deletion breakpoints. The nr2003 deletion was formed by cleavage of wild-type hop-1 sequences either after bp 2306 and 3502 or after bp 2307 and 3503.

FIG. 13 shows the relative functions of mutations which may be identified using the nematodes and methods of the invention.

DESCRIPTION OF THE PREFERRED EMBODIMENTS

I. Creation of nematodes for the study of Alzheimer's Disease

To explore the functions of the sel-12 and hop-1 presenilins, we used a reverse genetic strategy to generate sel-12 and hop-1 deletion mutations. Our analysis of hop-1;sel-12 double mutants provides genetic evidence that sel-12 and hop-1 function redundantly to promote Notch-pathway signaling and reveals a requirement for maternal expression of hop-1 and sel-12. In addition, we describe results of genetic screens to isolate suppressors of combinations of sel-12, hop-1 and spe-4 mutations and screens for mutations which phenocopy combination of sel-12, hop-1 and spe-4. The nematodes used in these screens may also be used to screen for compounds which prevent, ameliorate, or exacerbate AD.

Results

A hop-1 deletion mutant in a wild-type genetic background has no striking phenotype. To demonstrate that hop-1 is expressed, we isolated hop-1 cDNAs and performed reverse transcriptase-PCR and sequence analyses.

Figure 1A:
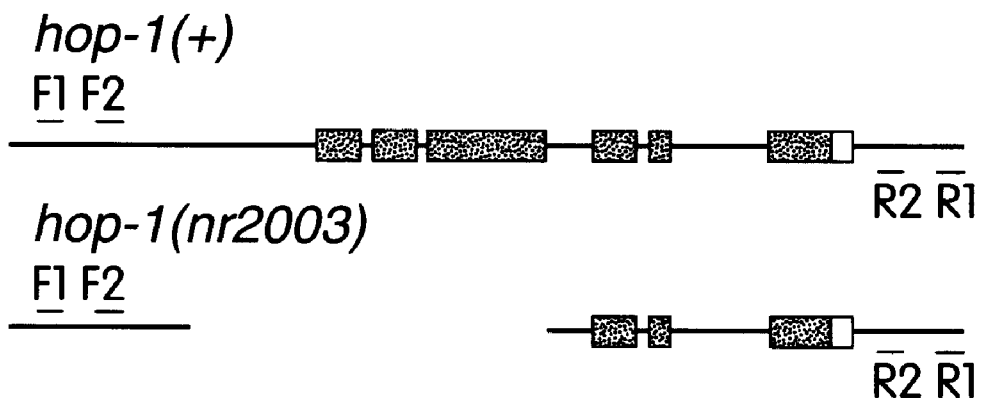
FIGS. 1A–1B show schematic representations of the hop-1 and sel-12 loci in wild-type (+) and deletion-containing animals. Black boxes represent coding sequences, open boxes represent 3' untranslated sequences and lines represent extragenic sequences (Levitan et al., Nature 377:351–354, 1995; Li et al., Proc. Natl. Acad. Sci. USA 94:12204–12209, 1997). A) The extent of the nr2003 deletion is indicated by the gap. F1, F2, R1, and R2 denote the approximate locations of the nested PCR primers used to identify the nr2003 deletion. B) The extent of the nr2011 deletion is indicated by the gap. Primers used to identify the nr2011 deletion are designated as in FIG. 1A.
Figure 1B:
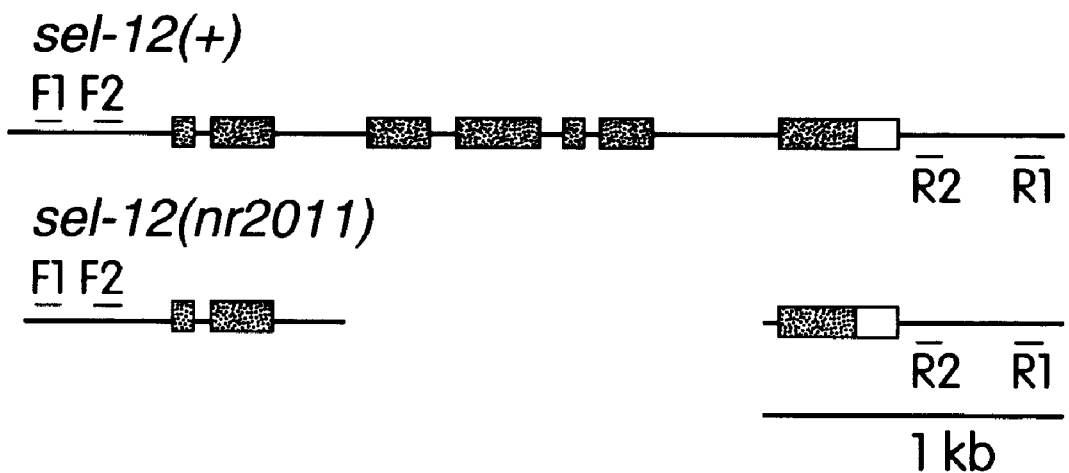
Figure 2A:
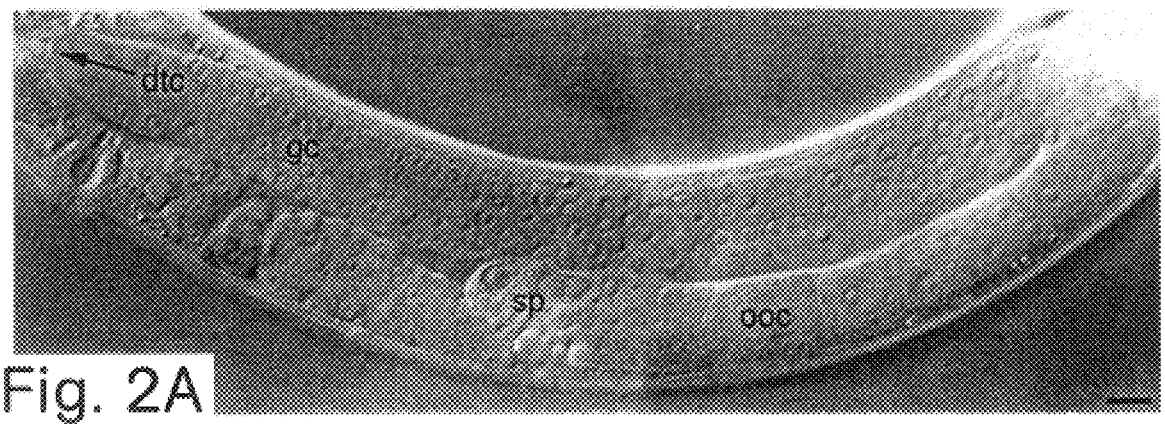
FIGS. 2A–2D show the germ line and somatic gonads of hop-1;sel-12 animals display Glp-1 and Lin-12-like phenotypes. Shown are differential interference contrast (DIC) photomicrographs of wild-type (FIGS. 2A and 2C) or strain A hop-1;sel-12 (FIGS. 2B and 2D) hermaphrodites.
Figure 2B:
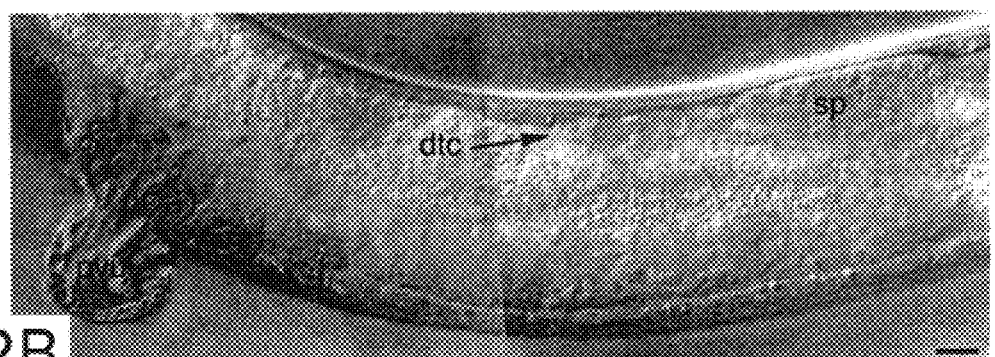
Figure 2C:
Figure 2D:
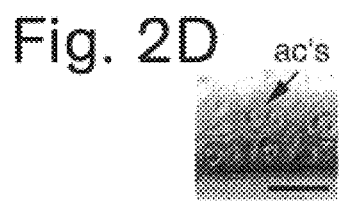

A deletion in the hop-1 locus was then generated using a reverse genetic approach described below. Deletion libraries representing 460,000 mutagenized genomes were screened by PCR with primers flanking the hop-1 coding region (see Example 1). Animals containing the deletion nr2003 were recovered from a library that had been mutagenized with UV-trimethylpsoralen. Sequence analysis revealed a 1196 bp deletion beginning 434 bp upstream of the hop-1 translation start site and ending in the third intron (FIG. 1A). hop-1 (nr2003) homozygotes were viable and had no apparent morphological or behaviorial defects. However, at 150 C, hop-1 (nr2003) hermaphrodite brood size was reduced by 44% relative to wild-type (147±288 vs. 262±130). Unlike mutations in sel-12 (Levitan et al., Nature 377:351–354, 1995), hop-1(nr2003) did not noticably suppress a lin-12 gain-of-function allele n950sd.

hop-1 and sel-12 are redundant for maternal and zygotic functions in embryogenesis and germline proliferation. To examine whether hop-1 and sel-12 have redundant functions, we generated a hop-1;sel-12 double mutant. First, we isolated a sel-12 deletion mutant (nr2011) using the same reverse genetic strategy that was used to generate hop-1 (nr2003; see below). Deletion libraries representing 1,100,000 genomes were screened with sel-12-specific primers (see Example 1). Animals containing the deletion nr2011 were recovered from a library mutagenized with ENU. Sequence analysis revealed a 1426 bp deletion starting in the second intron and ending in the sixth intron (FIG. 1B); splicing of the second exon to the seventh exon, if it occurred, would cause a frameshift. Thus, sel-12(nr2011) is predicted to encode a severely truncated protein containing the N-terminal 82 amino acids of Sel-12 followed by 23 novel amino acids. Like previously described sel-12 mutations (Levitan et al., Nature 377:351–354, 1995), sel-12 (nr2011) caused a highly-penetrant egg-laying defective (Egl phenotype and suppressed lin-12(n950sd).

hop-1;sel-12 double mutant animals displayed new phenotypes not seen in either single mutant. Furthermore, the phenotype of double mutant animals depended on maternal genotype (Table 1). Strains of three different genotypes (designated A, B, and C) that segregate hop-1;sel-12 progeny were generated. Strain A, of the geneotype hop-1/+; sel-12, segregates hop-1;sel-12 double homozygotes that are sterile. In contrast, strain B, of the genotype hop-1;sel-12/+, segregates hop-1;sel-12 homozygotes that have a maternal-effect embryonic lethal (Mel) phenotype and are Egl (the "Bag of Dead Eggs" phenotype). Strain C, of genotype hop-1/+; sel-12/+, also segregates hop-1;sel-12 homozygotes that are both Mel and Egl (Table 1). We interpret these results as follows: first, a complete absence of maternal and zygotic hop-1 and sel-12 function results in embryonic lethality; second, in the absence of sel-12 function, maternal expression of hop-1 is sufficient for normal embryogenesis but not for normal germline development, resulting in sterility; and third, in the absence of hop-1 function, maternal expression of sel-12 is sufficient for normal embryogenesis and germline development.

The phenotypes displayed by hop-1;sel-12 double mutants can be attributed to defects in GLP-1/LIN-12 signaling. The sterile and Mel phenotypes displayed by hop-1;sel-12 progeny are reminiscent of defects seen in glp-1 loss-of-function (lf) mutants. Normally, a cell-cell interaction between the distal tip cell and germ cells, mediated by the GLP-1 receptor, induces germ cells to proliferate (Austin et al., Cell 51:589–599, 1987). Strong glp-1(lf) mutants produce a reduced number of sperm, no oocytes, and hence are sterile due to the failure of their germ cells to respond this proliferative signal (Austin et al., Cell 51:589–599, 1987). Similarly, the gonads of hop-1;sel-12 progeny that segregate from strain A contain 50–100 sperm but neither oocytes nor undifferentiated germ cells (Table 1, FIGS. 2A–2D).

Weak glp-1(lf) mutations have revealed additional roles for maternally-10 contributed glp-1 in early embryonic development (Austin et al., Cell 51:589–599, 1987; Priess et al., Cell 51:601–611, 1987; Mello et al., Cell 77:95–106, 1994). At the 4-cell embryo stage, glp-1 is required for proper fate-specification of the blastomere ABp (Mello et al., 77:95–106, 1994). Similarly, we found that inviable hop-1;sel-12 mutant embryos (derived from strain B) lack intestinal valve cells (FIG. 3A–C).

A second requirement for glp-1 occurs at the 12-cell embryo stage (Priess et al., Cell 51:601–611, 1987; Mello et al., Cell 77:95–106, 1994). At this stage, descendants of ABa are induced to produce pharyngeal tissue as a result of a glp-1-dependent cell-cell interaction. In glp-1 mutant embryos, this interaction fails and the anterior lobe of the pharynx is not formed. However, the posterior lobe of the pharynx is present, because the cells that comprise it are descended from a different blastomere, MS, that does not require a glp-1-mediated interaction to produce pharyngeal cells (Priess et al., Cell 51:601–611, 1987). Like glp-1 mutant embryos, inviable hop-1;sel-12 mutant embryos lack anterior pharynx but form posterior pharynx. hop-1;sel-12 embryos were stained with an antibody specific for pharyngeal myosin (see Example 1). The amount of pharyngeal tissue seen in these embryos was reduced relative to that seen in wild-type embryos and was comparable to that seen in gap-1 mutant embryos (FIG. 3D–F). Furthermore, as with glp-1 mutant embryos (Priess et al., Cell 51:601–611, 1987), no pharyngeal tissue was observed in hop-1; sel-12 embryos in which the posterior pharynx had been eliminated by killing descendants of the MS blastomere. Taken together with the results showing the absence of intestinal valve cells, these data suggest that cell-fate defects similar to those observed in glp-1 mutant embryos occur in inviable hop-1;sel-12 mutant embryos.

It was useful to demonstrate that the new phenotypes uncovered in hop-1;sel-12 mutants were due to loss of hop-1 activity. We used RNA-mediated interference (RNAi) (Fire et al., Nature 391:806–811, 1998) to show that disruption of hop-1 function in sel-12 mutant animals can lead to defects that are similar to those observed in hop-1(nr2003); sel-12 double mutant animals. Antisense hop-1 RNA was injected into both wild-type and sel-12 mutant hermaphrodites (see Example 1). Progeny from injected sel-12 mutant animals included both sterile animals with a germline proliferation (Glp) defect and dead embryos, whereas progeny from injected wild-type animals had no apparent defects (brood size was not scored). These results argue that the defects observed in hop-1(nr2003); sel-12 mutant animals are dependent on the nr2003 deletion.

In addition to Glp-1-like defects, some hop-1;sel-12 mutants display Lin-12-like defects. lin-12(lf) mutants exhibit numerous cell-fate changes (Greenwald et al., Cell 34:435–444, 1983). One well-characterized cell-fate change occurs in the hermaphrodite somatic gonad. During normal larval development, lin-12-mediated signaling between the somatic gonad primordium cells Z1.ppp and Z4.aaa ensures that they develop into two distinct comatic gonadal cell types, an anchor cell (AC) and a ventral uterine precursor cell (VU). however, in lin-12(lf) mutants, both Z1.ppp and Z4.aaa develop into ACs (Greenwald et al., Cell 34:435–444, 1983). We found that hop-1;sel-12 mutant animals segregating from strain A, but not from strain B, also have two ACs (Table 1, FIGS. 2A–2D). Furthermore, hop-1;sel-12 mutant animals segregating from strain A have a highly-penetrant protuding vulva phenotype that closely resembles that seen in lin-12(lf) mutants ((Greenwald et al., Cell 34:435–444, 1983) and FIGS. 2A–2D).

Since hop-1;sel-12 mutant animals from strain A display both Glp-1-like and Lin-12-like defects, we reasoned that they might also exhibit phenotypes similar to those of lin-12;glp-1 double mutant animals. lin-12; glp-1 double mutants display more severe defects than either single mutant, due to partial redundancy of lin-12 and glp-1 functions (Lambie et al., Development 112:231–240, 1991). The lin-12; glp-1 double mutant phenotype, termed lag (lin-12 and glp-1), is a zygotic larval lethal with characteristic cell fate defects. We did not detect any Lag-like animals among 485 progeny segregating from hop-1/+; sel-12 hermaphrodites.

Genetic suppressors of hop-1;sel-12 are much more difficult to isolate than are suppressors of sel-12 alone. To identify genes that interact with C. elegans presenilin genes, we carried out three screens to suppress phenotypes caused by sel-12 and hop-1 mutations. The first screen was designed to isolate suppressors of the Egl phenotype of sel-12 mutant hermaphrodites (see Example 1). From 35,000 genomes screened, 56 independent suppressed lines were obtained, a frequency of 1 in 625 genomes.

The second screen was designed to isolate suppressors of the sterile phenotype of hop-1;sel-12 double mutants derived from strain A. This screen was complicated by the fact that the double mutant could not be maintained in a homozygous state. To circumvent this difficulty, we took advantage of mutations that confer resistance to the anthelminthic agent ivermectin, using this to select for the one-quarter hop-1;sel-12 doubly homozygous progeny that segregate from a hop-1/+; sel-12;sel-12 parent (see Example 1). From 77,000 genomes screened, no suppressors were identified.

The third screen was designed to isolate suppressors of the Egl phenotype of hop-1/+; sel-12/sel-12 hermaphrodites. This screen offers several advantages compared to the screen for suppressors of the sel-12 Egl phenotype in a hop-1(+) background. First, any suppressor mutations obtained can rapidly be examined for their ability to suppress the hop-1;sel-12 sterile phenotype by examining hop-1;sel-12 self-progeny of suppressed hermaphrodites. Both strong suppression of the sterile phenotype, resulting in fertility, and weak suppression, resulting in an increase in the number of germ cells or the presence of oocytes, could be detected. Second, the Egl defect exhibited by hop-1(nr2003)/+; sel-12 (nr2011)/sel-12(nr2011) hermaphrodites is stronger than that of sel-12(nr2011) hermaphrodites: 100% of hop-1 (nr2003)/+;sel-12(nr2011) sel-12(nr2011) hermaphrodites lay no eggs, whereas 97% of sel-12(nr2011) hermaphrodites lay no eggs and the remaining 3% lay a small number of eggs, typically fewer than five. Therefore, we anticipated that suppressors of the Egl phenotype of hop-1/+; sel-12/sel-12 animals might be more difficult to obtain than suppressors of the Egl phenotype of sel-12 animals. Because suppressors of sel-12 animals were frequent, a more stringent screen for suppression using the hop-1/+;sel-12/sel-12 strain would be useful for choosing which suppressors to characterize further. From 30,000 genomes screened using the hop-1/+;sel-12/sel-12 strain, nine independent suppressed lines were obtained, a frequency of 1 in 3333 genomes. This frequency is indeed lower than that obtained using the sel-12 strain. We have not detected suppression of the sterility defect of hop-1;sel-12 animals in any of these lines.

Summary of Experimental Results

The finding that hop-1; sel-12 mutant animals display Glp-1 and Lin-12 defects not observed in either single mutant indicates that hop-1 and sel-12 function redundantly to promote Notch-pathway signaling.

Suppressors of the sel-12 single mutant are found much more readily than are suppressors of the hop-1; sel-12 double mutant. There are several possible explanations for the marked difference between the ease with which we found suppressors of the sel-12 Egl defect and our inability to find suppressors of the hop-1;sel-12 sterility. First, sel-12 Egl suppressors might promote egg-laying competence by activating hop-1 function. Second, they might potentiate glp-1/lin-12 signaling supported by wild-type levels of hop-1 activity, but unable to bypass the more severe reduction in glp-1/lin-12 signaling associated with a complete lack of presenilin function. Third, sel-12;egl-1 suppressors might affect egg laying through a mechanism independent of glp-1/lin-12 signaling. Finally, suppressors of the sel-12 Egl defect might be expressed in the soma but not in the germ line.

Our experiments conducted in *C. elegans* have revealed that presenilins facilitate Notch receptor function, although the precise role of presenilins in promoting Notch signaling has not yet been identified.

The relationship between the proposed role of presenilins in AD pathogenesis-affecting the proteolytic processing of APP and their role in promoting Notch receptor function-is not yet clear, but may be addressed using our model system. Intriguingly, it has recently been demonstrated that the Drosophila Notch receptor undergoes proteolytic processing by Kuzbanian, an ADAM-family protease, en route to the cell surface, and that this cleavage event is required for Notch to function appropriately. Thus, two proteins with which presenilins are proposed to interact with (directly or indirectly), APP and the Notch receptor, are both undergo proteolytic processing while trafficking to the plasma membrane. Thus, presenilins might regulate Notch receptor processing in a manner analogous to their regulation of APP processing. An understanding of how presenilins affect Notch receptor activity is thus be relevant to understanding how presenilin dysfunction causes AD.

Figure 12:
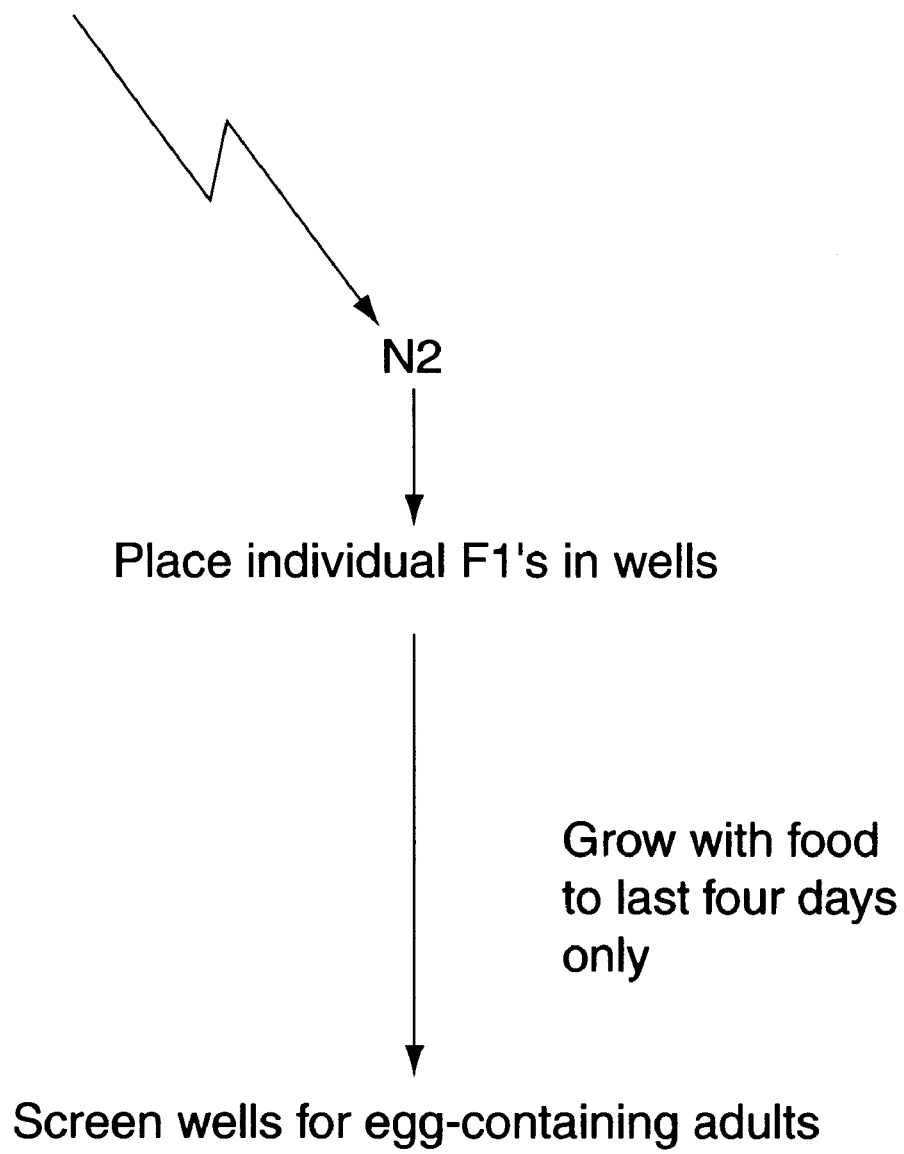
FIG. 12 shows a schematic of a screen of the invention.
Figure 14:
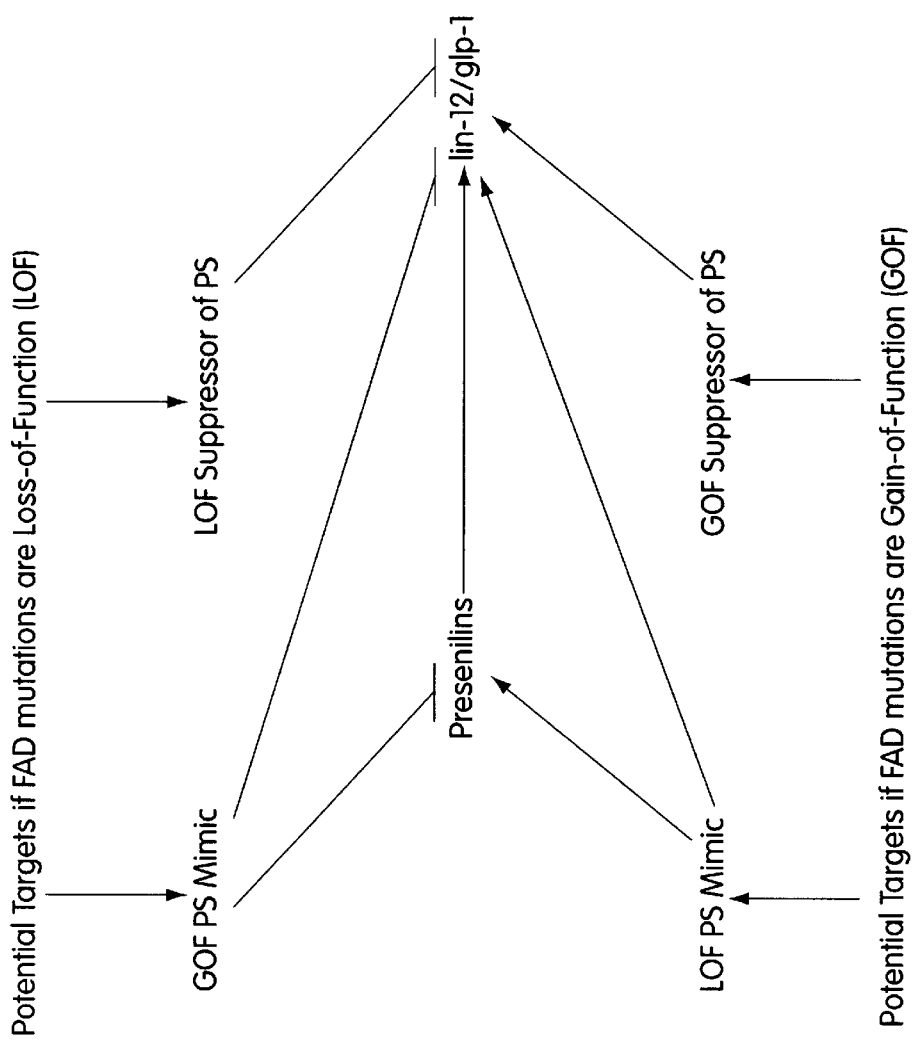
FIG. 14 is a schematic showing the potential interactions between gene products and genes which may be detected using the methods of the invention.

Isolation of suppressors of hop-1, sel-12, and spe-4 and isolation of molecules acting in the AD pathway Our results suggest specific screens for the identification of targets for the treatment of AD (see FIGS. 12 and 13, and the Examples below). If, for example, the PS(FAD) mutations are loss-of-function, negative regulators of a presenilin pathway are potential drug targets. Thus, suppressors of presenilin deletion knockouts will provide the following: 1) mutations that suppress presenilin deletion knockouts and bypass the need for presenilins should identify genes that function either downstream of presenilins or in a parallel pathway; 2) recessive mutations that confer suppression are likely to be loss-of-function mutations and should identify genes that are negative regulators of a presenilin pathway or a parallel pathway; and 3) chemical suppressors are likely to inhibit negative regulators of a presenilin pathway or a parallel pathway.

If, on the other hand, the PS(FAD) mutations are gain-of-function, positive regulators of a presenilin pathway are potential drug targets. Suppressors of presenilin deletion knockouts can provide dominant mutations that suppress presenilin deletion knockouts such dominant mutations may be gain-of-function and thus identify positive regulators of a presenilin pathway, or a parallel pathway.

All deletion suppressor screens conducted to date have been F2 screens which have enabled isolation of both recessive and dominant mutations. (F3 screens are also possible.) Preliminary evidence suggests that some hop-1/+;sel-12 suppressors may act semi-dominantly or dominantly.

If any suppressors have phenotypes alone, one may suppress that phenotype, thus providing targets in the opposite direction of the pathway.

Suppressors of presenilin gain-of-function phenotypes will, in turn, yield recessive mutations that confer suppression and are loss-of-function. Such mutations should thus identify positive regulators of presenilins and chemicals that confer suppression would likely inhibit positive regulators of presenilins.

Genetic Screens for Mutants That Phenocopy Presenilin Deletions

Phenocopying presenilin loss-of-function phenotypes will provide the following information: recessive mutations that phenocopy presenilin loss-of-function phenotypes are likely to be loss-of-function themselves, and thus identify positive regulators of presenilins (or are presenilin mutants) and chemicals that phenocopy presenilin loss-of-function phenotypes likely inhibit presenilins or positive regulators of presenilins. A pilot genetic screen of 4800 genomes looking for "bags of dead eggs" phenotype displayed by some hop-1;sel-12 hermaphrodites yielded eight potential mutants.

To find further genes which positively regulate one or more presenilin genes one may mutagenize worms and look for animals that phenocopy the presenilin mutants (e.g. have the phenotype of a single, double, or triple mutant, as described herein).

The first method is to mutagenize wild-type worms and look for "bags of dead eggs" to identify genes that positively regulate hop-1 and sel-12. If such a gene also regulates spe-4 they would be missed due to a Spe sterile phenotype. One may validate the above screen by analyzing dead embryos for Glp-like defects and testing for suppression of lin12(gf).

A second method to achieve the above goal is to identify mutagenized wild-type worms and look for bags of oocytes that become bags of dead eggs when mated to wild-type males, phenocoping the triple a presenilin mutant. Such a screen could identify genes that positively regulate hop-1, sel-12 and spe-4, a more restrictive screen, then the above screen. We predict that mutants will retain oocytes in the uterus, necessitating looking for striping of oocytes in the gonad on plates lacking oocytes on the plate.

A third method for identifying genes which phenocopy a presenilin deletion is to mutagenize hop-1 worms and look for "bags of dead eggs." This is less stringent screen then the screen for wild-type worms with "bags of dead eggs" (above) and, in addition, identify positive regulators of sel-12 only and new sel-12 mutations. This adaptation would miss genes that regulate sel-12 and spe4. However, such a gene would fail to interact with hop-1 and so it might be picked up in the screen for "bags of dead eggs" (above).

A fourth approach is to mutagenize sel-12 worms and look for Glp steriles. This screen is less stringent, but could isolate everything in the first two above screens, as well as positive regulators of hop-1 only and new mutations in hop-1, glp-1, lag-1, and lag-2.

Screens for Compounds That Phenocopy Presenline Deletions

To determine if a compound will affect one, two, or all three presenilins and to determine at what stage a compound should be added in order to see Glp sterile, Spe sterile, Egl and Mel phenotypes one may do the following: 1) add compound to wild-type worms (L1s and L3s/L4s or a mixed population) and look for Glp steriles and bags of dead eggs or Glp/Spe steriles and Spe steriles (this assumes a chemical affects HOP-1 and SEL-12 (directly or indirectly), but may or may not affect SPE-4); 2) add the compound to wells of L3/L4 hop-1 mutant or wild-type worms and look for "bags of dead eggs" in the hop-1 wells, but not the corresponding wild-type wells (this assumes a compound affects SEL-12, but not HOP-1 or SPE-4); 3) substitute human PS1 for sel-12 or for hop-1/+;sel-12, then do screen of 1), above (if presenilins are targets, then humanizing the worms in this way improves the screen); or 4) add compounds to wells of L3/L4 sup (hop-1/+;sel-12 Egl sup) mutant or wild-type worms and look for "bags of dead eggs" in the wild-type wells, but not in the sup wells.

II. Reverse Genetics Strategy

We have developed a technique for the rapid isolation of new strains of nematodes that have a deletion in essentially any gene or other region of choice. This technique provides a rapid method for reverse genetics in this powerful model organism.

In our reverse genetics strategy, large numbers of mutagenized worms are distributed into an ordered array of separate cultures, which are grown to generate numerous progeny. Genomic DNA is prepared from an aliquot of each culture of worms, while the remaining worms are stored away as viable sibling populations. PCR is then used to screen for deletions within a targeted gene, using primers. Primers may readily be designed, for example, from publicly available DNA sequence generated by the *C. elegans* Genome Sequencing Consortium. Amplicons from a template bearing deleted DNA within the targeted region will be shorter and thus identify a specific address within the ordered array of cultures. "Knockout" animals bearing such deletions are then isolated from that specific culture, and studied with the full range of biological approaches to elucidate the function of the targeted gene.

We have successfully identified mutations in every region of choice which has been targeted to date. Our reverse genetics technology provides new tools for functional genomics approaches Such approaches may be pursued together with standard genetic, molecular, and pharmaceutical methods in order to illuminate the function and pathway of conserved genes that are involved in human diseases and other diseases of interest.

Protocol for General Mutagenesis:

1. The first step is to mutagenize the nematodes. Deletions have been identified following mutagenesis with EMS, ENU, diepoxyoctane and UV/trimethylpsorlalen (see the examples, below). We believe a variety of other mutagens known to mutagenize the nematode genome may also be employed at this step. We estimate the efficiency of mutagenesis by determining the number of ivermectin-resistant mutants in the F2 generation.

2. Following mutagenesis, cultures are started by seeding twenty F1 worms into each well of a microtiter plate. Following growth of the cultures, each well contains approximately 2000 F2 larvae. Our standard-sized library contains forty-eight 96-well microtiter plates, representing 192,000 mutagenized genomes. Thus far we have screened for deletions using seven such libraries, three mutagenized with UV/TMP, two with EMS and one each with ENU, and diepoxyoctane.

3. For each well, one-third of the worms are separated into two equal portions and digested with worm lysis buffer to produce two sets of DNA extracts. The remaining two-thirds of the worms are frozen.

4. For the primary screen, the two sets of DNA extracts are screened in parallel. We screen in duplicate to avoid cases where a deletion has occurred in a single F2 worm. For each set of DNA extracts, an aliquot of the extract from each well of a 96-well plate are mixed, generating a pool representing 4,000 mutagenized genomes. Our PCR protocol is based on a modification of protocols used for Tc1 mutagenesis (See e.g., in *Caenorhabditis elegans*: Modern Biological Analysis of an Organism, Methods in Cell Biology, Volume 48, pp. 59–80 incorporated herein by reference) and uses a nested set of primers generally placed 3–5 kb apart, AmpliTaq Gold (Perkin-Elmer), and approximately 35 cycles of amplification are generally used. For most of our screening, we adjust the extension times (usually 2–3 min) such that a faint wild-type band is generated. We have also used extension time such that no wild-type band is generated. Once a potential deletion band has been identified by its altered size, the pool is tested four more times to determine whether a deletion band is actually present in the pool. After a deletion band has been replicated, a secondary screen is performed on pools of row and columns from the microtiter plate to identify the well containing the deletion and hence the well of frozen animals containing nematodes carrying the deletion.

5. Frozen worms from the well with the deletion are thawed (about 500 animals are usually recovered), cloned, and screened by PCR for animals carrying the deletion.

6. The worm having the desired deletion may then be characterized genetically and biochemically and used for therapeutic drug screening and research protocols.

Yield

This method has been used to isolate worms carrying deletion mutations in multiple genes. The average frequency of successful isolation is about one deletion from 400,000 genomes screened. With primers set 3–3.5 kb apart, most deletions detected are between 500 and 1500 bp size. Larger deletions have been detected with primers set 5 kb apart.

Frequency

Among the thawed worms, one would expect 3 in 80 animals to carry a viable deletion mutation ($1/20 \times 3/4$) and 1 in 30 animals to carry a lethal deletion mutation ($1/20 \times 2/3$). However, in practice we have found that it is advisable to screen a minimum of 250 animals since the frequency of animals carrying deletions can vary.

EXAMPLES

The following examples are meant to illustrate, not limit the invention.

Example 1

Materials and Methods

General methods and strains.

Nematode strains were cultured using standard techniques (Brenner, Genetics 77:71–94 1974). except that strains used to generate the deletion libraries were cultured in liquid, as described below. All strains were grown at 20° C. unless noted otherwise. *C. elegans* variety Bristol strain N2 was the parent of all strains used in these studies (Brenner, Genetics 77:71–94 1974). Alleles used were: LGI: unc-73(e936), hop-1(nr2003), avr-14(nr391), dpy-5(e61); LgIII: lin-12 (n950sd), glp-1(q231ts); LGV: avr-15(nr395); LGX: egl-17 (e1313), pha-2(ad472), sel-12(nr2011), unc-1(e538), dpy-3 (e27)

Generation of the deletion libraries.

For mutagenesis, late fourth-larval-stage (L4) N2 hermaphrodites were either treated with one of the following three chemical mutagens for 4 hours: ethyl methane sulfonate (EMS) at 0.25%, ethylnitrosourea (ENU) at 0.4 mM or diepoxyoctane (DEO) at 1 mM (Anderson, in Caenorhabditis elegans: Modem Biological Analysis of an Organism, eds. Epstein and Shakes, Academic Press, Inc., San Diego, 48:31–58, 1995; and refs within), or exposed to UV light (366 nm) at 3.5 mW/cm$^2$ for 15 to 30 seconds after a 20 minute incubation in 30 µg/ml trimethylpsoralen (Yandell et al., Proc. Natl. Acad. Sci. USA 91:1381–1385, 1994). $F_1$ eggs derived from mutagenized hermaphrodites were collected for 4 hours, then allowed to hatch for 16 hours. For each deletion library, hatched larvae were distributed to 48 96-well polystyrene microtiter plates at about 20 larvae per well in NGM medium (Wood, Cold Spring Harbor Laboratory Press, Plainview, N.Y., 1988) with 1% (v/v) E. coli HB101 as food. Each library thus represents approximately $2 \times 10^5$ mutagenized genomes. Worms were cultured in wells for about five days until no food remained, at which point approximately 100 $F_2$ progeny per $F_1$ animal had been produced. Half of the worms in each well were removed and used to make genomic DNA. Of these, half were transferred to wells of V-bottom 96-well microtiter plates and half were pooled; for each of the original microtiter plates, worms from all wells were combined into a single pool (plate pools). Worms in V-bottom wells were digested with 10 µl worm lysis buffer (Williams et al., Genetics 131:609–624, 1992) for up to 16 hours. Plate pools were digested for 4 hours with 0.4 ml plate pool lysis buffer (100 mM NaCl, 100 mM Tris-Cl (pH 8), 50 mM EDTA, 1% SDS, 1% β-mercaptoethanol and 100 µg/mL proteinase K). The worms remaining in the original microtiter plates were frozen using standard methods and served as viable stocks (Wood, Cold Spring Harbor Laboratory Press, Plainview, N.Y., 1988).

Identification and recovery of hop-1 and sel-12 deletion mutants.

Figure 5:
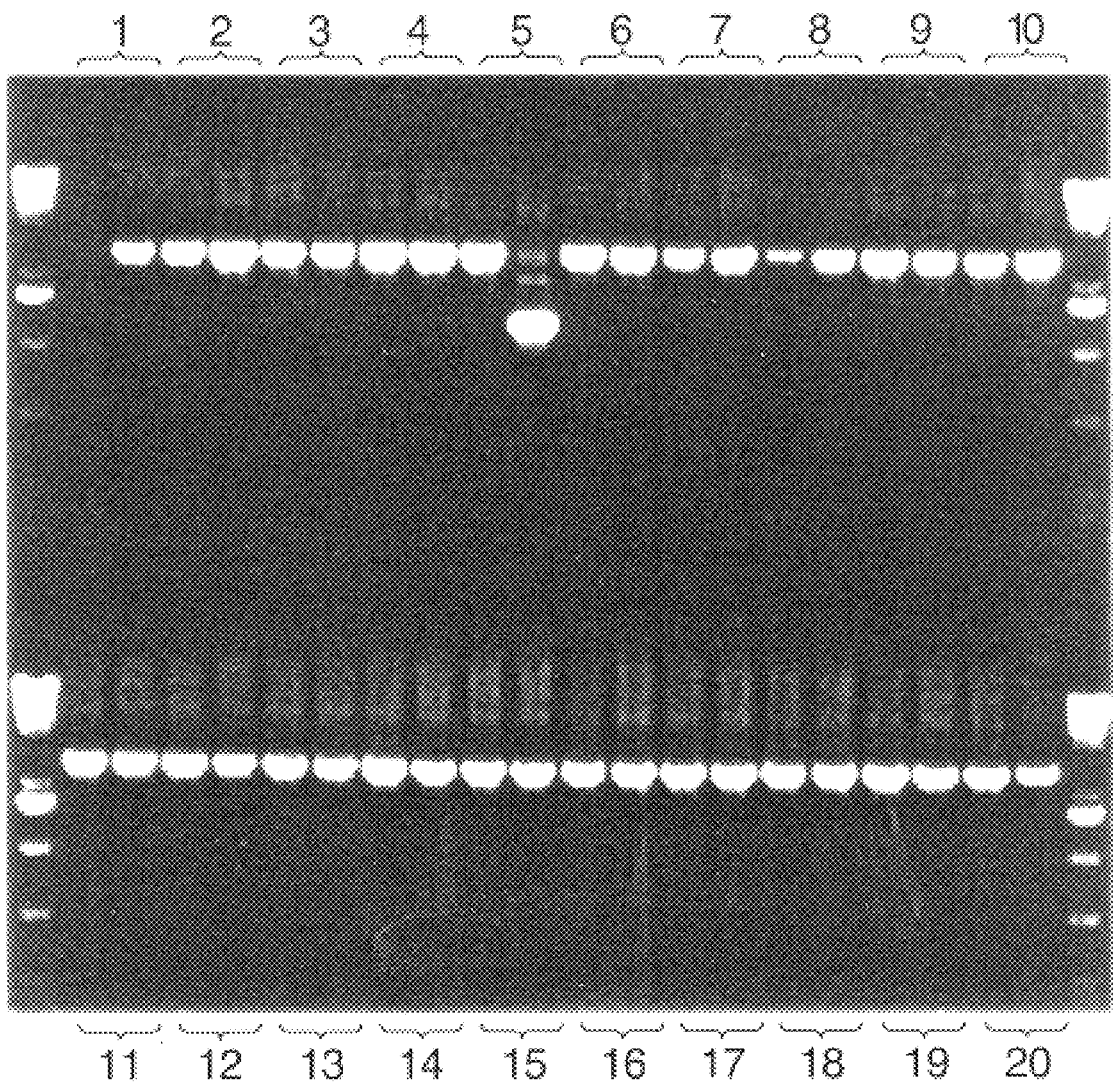
FIG. 5 shows gel pictures of samples from an initial PCR screen of *C. elegans* mutagenized with ethyl nitroso urea (ENU). Pools of worm lysates were screened by nested PCR using primers sel-12.F1, sel-12.F2, sel-1.R1 and sel-1.R2. Two independent sets of DNA were assayed for each pool. The wild-type 2.7 kb product is seen in every lane. Pool #5, set 2, also shows a potential 1.3 kb deletion (GIBCO-BRL 1 kb ladder DNA molecular wight standards).
Figure 6:
FIG. 6 shows a gel demonstrating that worms containing deleted DNA were recovered from frozen worm stocks. Plate #5, well H7, was thawed and transferred to nematode growth medium (NGM) plates seeded with E. coli. Single animals were cloned on fresh NGM plates and the progeny were collected, lysed, and assayed for the presence of a DNA deletion by PCR using primer pairs identical to those described in FIG. 8. DNA from well H7 was included as a positive control. DNA from two worms, labelled 11 and 31, are positive for the 1.3 kb deletion product (GIBCO-BRL, 1 kb ladder DNA molecular weight standards). The strain derived from progeny of the animal labelled 11 bore the deletion named sel-12(nr2011).
Figure 7:
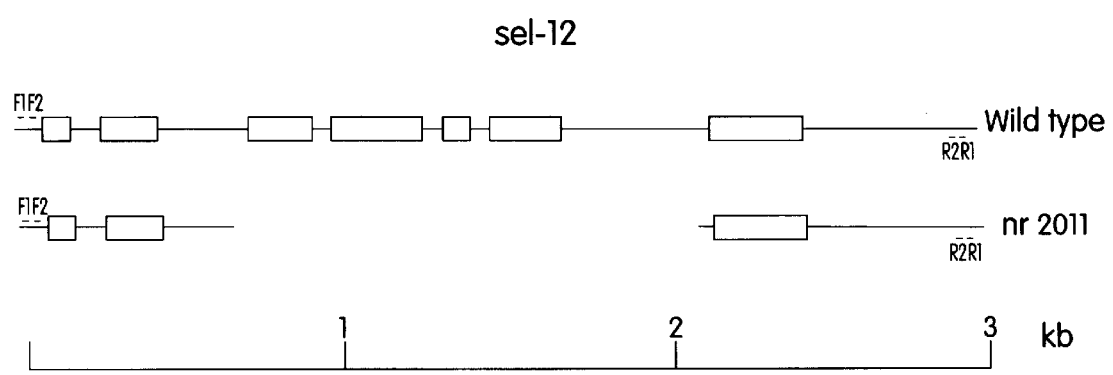
FIG. 7 shows a schematic representation of the sel-12 genomic region of wild-type and the nr201 I-mutants. Boxes represent exons, lines between boxes represent introns. The approximate locations of the PCR primers used in the screens are indicated by short horizontal bars and primer names. The location of the nr2011 deletion is indicated by the gap.
Figure 9:
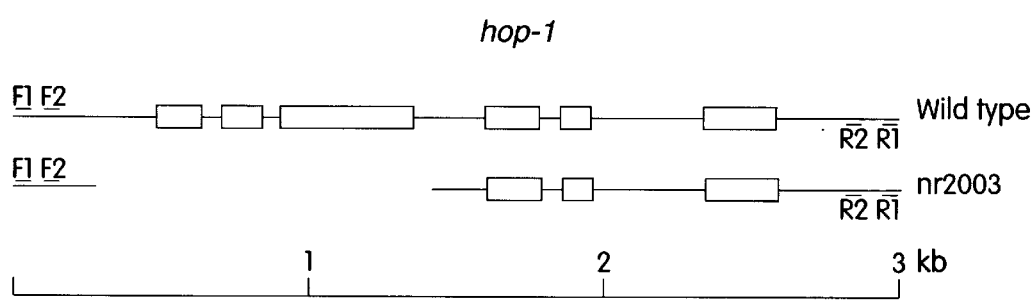
FIG. 9 shows a schematic representation of the genomic region of predicted wild-type hop-1 and hop-1 (nr2003) deletion genomic regions. Boxes represent exons and lines represent introns. The approximate locations of the PCR primers used in the initial screening are indicated by short horizontal bars and primer names. Location of the nr2003 deletion is indicated by the gap.

Plate pools from multiple libraries were screened for deletions using nested polymerase chain reaction (PCR) primers specific for genomic sequences flanking the hop-1 or sel-12 coding regions (see FIG. 5). Primer pairs were chosen such that they amplified wild-type products ranging from 2.5 to 3.5 kb in size. Primer sequences are shown in Tables 2 and 3. The extension time was determined empirically for each primer pair such that a faint wild-type product was amplified reproducibly. Plate pools that gave rise to a deletion product were rescreened in quadruplicate to eliminate false positives. In cases where a pool was confirmed as positive, DNA from each well comprising that pool was screened individually by PCR. Once the specific well containing the deletion was identified, the corresponding well of worms was thawed and the animals recovered. Survivors from each frozen well were transferred clonally to plates. Hermaphrodites were cultured until they laid eggs and then genotyped by single-worm PCR (Williams, et al., Genetics 131:609–624, 1992). Homozygous lines were established from the self-progeny of hermaphrodites containing the deletions. Sequence analysis of PCR products indicated that the hop-1 (nr2003) deletion is 1196 bp and extends from bp #23,744 or 23,743 to 22549 or 22548, while the sel-12 (nr2011) deletion is 1426 bp and extends from bp #5533 ro 5534 to 6958 or 6959 (FIGS. 9–10). hop-1-related numbering refers to cosmid C18E3 (accession number AF000265) and sel-12-related numbering refers to cosmid F35H12 (accession number U41540). hop-1(nr2003) was outcrossed ten times to an unc-73(e936) dpy-5(e61) strain and sel-12 (nr2011) was outcrossed seven times to N2 before the genetic analyses described here were conducted.

RNA-mediated interference (RNAi) experiments. The template used to make RNA was an almost full-length hop-1 cDNA (lacking seven bp at the 5' end) inserted into the vector pCR2.1 (Invitrogen). The insert and flanking T7 promoter were amplified by PCR using M13 forward (−20) and reverse primers. Antisense hop-1 RNA was transcribed from this PCR product in vitro using T7 polymerase and a Riboprobe kit (Promega), then microinjected into N2 or sel-12(nr2011) hermaphrodite gonad arms at a concentration of 0.9 mg/ml using the method of Mello et al., Embo J. 10:3959–3970 (1991). None of the N2 hermaphrodites (0/10) had progeny that displayed any morphological or developmental abnormalities, whereas all of the sel-12 hermaphrodites (8/8) produced dead embryos and/or sterile progeny with a germline proliferation-defective phenotype.

Laser killing of cells in embryos and antibody staining.

Microscopy and laser microsurgery were as described by Bowerman et al., Cell 68:1061–1075 (1992), methanol/acetone fixation and freeze-crack permeabilization were as described by Miller et al., in Caenorhabditis elegans: Modern Biological Analysis of an Organism, eds. Epstein and Shakes, Academic Press, Inc., SanDiego, 48:365–394 (1995) and antibody staining and was as described by Shi et al., Genes & Dev 12:943–955 (1998). To visualize intestinal valve cells more easily, either the EMS or E blastomere was laser-killed to eliminate the intestine, as both the valve cells and the intestine stain with the J126 antibody (Mango et al., Development 120:2305–2315, 1994). For cell killing, early embryos were dissected from gravid N2, glp-1(q231ts), or hop-1;sel-12 parents. glp-1(q231ts) hermaphrodites had been shifted from 15° C. (permissive temperature) to 20° C. (non-permissive temperature for the maternal-effect lethal (Mel) phenotype (Austin et al., Cell 51:589–599, 1987)) 12–24h prior to dissection. After cell killing embryos were incubated for 6h at 22° C., then stained with the antibody. To visualize pharyngeal tissue, a monoclonal antibody (9.2.1) that is specific for pharyngeal myosin (Epstein et al., in Muscle Development, eds. Pearson and Epstein, Cold Spring Harbor Laboratory, Cold Spring Harbor, N.Y., pp. 7–14 1982) was used. glp-1(q231ts) embryos were taken from plates that had been incubated at 20° C. for 24h; hop-1;sel-12 embryos were dissected from the Egl parents.

Suppression of the Egl phenotype of sel-12(nr2011) and hop-1 (nr2003/+; sel-12(nr2011) animals. sel-12(nr2011) and hop-1(nr2003) avr-14(nr391)/unc-73(e936) dpy-5(e61); avr-15(nr395); sel-12(nr2011) hermaphrodites were mutagenized with EMS as described (Brenner, Genetics 77:71–94, 1974) and cultured individually on plates. Plates were screened 8 to 10 days later for the presence of $F_3$ eggs. Eggs were transferred to fresh plates and the animals that hatched from them were tested for egg-laying competence. Suppressor lines were established from single egg-laying competent $F_3$ animals.

Suppression of the sterile phenotype of hop-1 (nr2003); sel-12(nr2011) animals. hop-1(nr2003) avr-14(nr391)/unc-73(e936) dpy-5(eyl); avr-15(nr395) sel-12(nr2011) hermaphrodites were mutagenized with EMS as described (Brenner, Genetics 77:71–94, 1974). Mutagenized fertile non-Unc non-Dpy animals were cultured individually in wells of 96-well microtiter plates containing NGM medium with 1% (v/v) E. coli HB11 as food. When $F_2$ animals were first- or second-stage larvae, (typically 7–8 days later), the contents of each well were transferred to an agar plate containing NGM medium supplemented with 25 mM ivermectin. Plates were screened periodically for fertile animals starting one week later and continuing for up to four weeks. avr-14(nr391) and avr-15(nr395) single mutants are not resistant to ivermectin, but avr-14(nr391); avr-15(nr395) double mutants are highly resistant. Therefore, most of the animals that grew to adulthood on ivermectin-containing plates were of the genotype hop-1(nr2003) avr-14(nr391); avr-15(nr395); sel-12(nr2011) and were sterile. Animals containing a suppressor mutation were expected to be fertile and homozygous for the hop-1 chromosome.

Example 2

Construction of sel-12; hop-1 double mutant from nematodes having deletions in presenilin genes the two genes.

The power of the techniques of the invention are demonstrated by our subsequent ability to make a sel-12; hop-1 doubly deleted worm having a surprising phenotype which makes it particularity useful for drug discovery.

The hop-1 deletion constructed by our technique lacks a discernable phenotype in an otherwise wild-type background. Accordingly, absent the present technique, such a mutant would have been hard to obtain using standard genetic techniques.

Upon obtaining the hop-1 deletion mutant and the sel-12 deletion mutant we constructed the hop-1 (nr2003), sel-12 (nr2011) doubly deleted mutant. While sel-12 deletion mutants are Egl, we were surprised to find that the sel-12; hop-1 doubly detected strain has a maternal lethal phenotype. This indicates these two genes have at least partially redundant functions. Thus, the double mutant provides a nematode useful for improved screens. These screens may be used to identify suppressor mutations which, in turn, identify other genes in this Alzheimer's-related pathway. The screens may also be used to identify therapeutic compounds which ameliorate the effects caused by mutations in the presenilin genes.

We believe a spe-4; hop-1 doubly deleted worm, a spe-4; sel-12 doubly deleted worms and the sel-12; hop-1; spe-4 triply deleted worms (or parents capable of giving rise to eggs having these genotypes) will all be useful in the above described methods.

Figure 11:
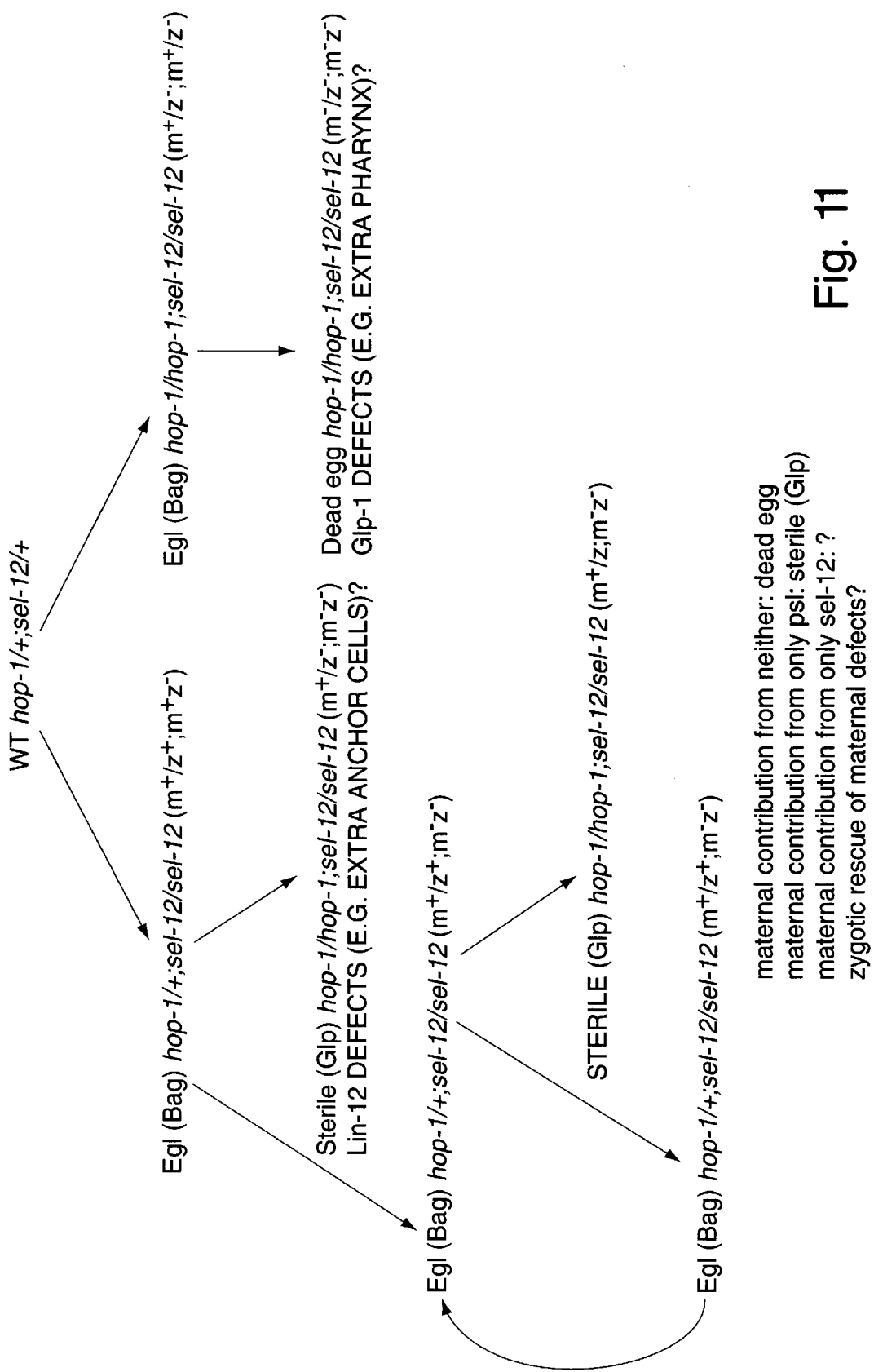
FIG. 11 shows a diagram of phenotypes from hop-1/+; sel-12/+ progeny.

FIG. 11 shows the expected progeny, with phenotypes, for a hop-1/+; sel-12/+ wild-type phenotype parent strain. Optimally, suppressors may be obtained by looking for revertants of the hop-1/hop-1;sel-12/sel-12 (m−/Z−; m−Z−) dead egg phenotype or the sterile phenotype of the genotypically identical (m+/Z−; m−; Z−) animals. Therapeutic compounds may be screened by providing the test compound at the appropriate stage (i.e., exposing the parent of the generation having the sterile or dead egg phenotype to the test compound), if necessary.

One skilled in the art of nematode genetics will recognize that dominant and negative linked markers, balancer chromosomes, and plating techniques may be employed to enhance the efficiencies of the methods, as needed or desirable.

Example 3

Genetic Screens for Alzheimer's Disease-Associated Genes

If the presenilin mutations which are causative for Alzheimer's are reduction-of-function mutations, then loss-of-function mutations which suppress presenilin reduction of function mutations in the worm will identify molecules whose inhibition could ameliorate the disease state in humans. Gain-of-function mutations which mimic presenilin reduction of function may also identify such molecules (see FIG. 13).

Suppression of presenilin loss-of function mutations spe-4 causes a defect in spermatogenesis. sel-12 causes an egg-laying defect. hop-1 causes a mild reduction in brood size. The hop-1; sel-12 double mutation results in different phenotypes depending on maternal genotype. If the mother of the animal was either hop-1/+; sel-12/+ or hop-1; sel-12/+, than the double mutant animal will be egg-laying defective and the eggs will die, a "Bag of Dead Eggs" phenotype. If the mother of the animal was hop-1/+;sel-12, then the double mutant animal will be Glp-Sterile. Additionally, a hop-1/+;sel-12 animal has a stronger egg-laying defect than that caused by sel-12 alone.

Specific screens are as follows.

We have conducted an F2 screen for suppressors of the Glp Sterile double mutant animals form the hop-1/+;sel-12 mothers. This screen could have recovered both recessive, semi-dominant, or dominant suppressors. In 77,000 genomes screened, 0 suppressors were identified.

One may conduct an F3 screen for suppressors of the Glp Sterile double mutant animals from the hop-1/+;sel-12 mothers. This screen could recover mutations which are materially-rescued, and therefore would not be identified in an F2 screen.

We have conducted an F2 screen for suppressors of the egg-laying defect of hop-1/+;sel-12 animals. This screen recovered recessive and semi-dominant mutations, and could have recovered dominant mutations as well. In 30,000 genomes screened, 9 suppressors were recovered.

One may conduct an F1 screen for suppressors of the egg-laying defect of hop-1/+;sel-12 animals. This screen will recover semi-dominant and dominant mutations, which could define either gain-of-function, haplo-insufficient or dominant-negative mutations.

One may conduct an F2 screen for suppressors of the "Bag of Dead Eggs" double mutant animals from the hop-1;sel-12/+ and hop-1/+;sel-12 mothers. This screen could recover recessive, semi-dominant, or dominant suppressors. If suppressors are identified, an F 1 screen will be done to identify only suppressors which act dominantly or simi-dominantly. If suppressors are rare, than an F3 screen may be done to identify mutations which are maternally-rescued.

Screens which mimic presenilin loss-of-function

To identify targets involved in both hop-1 and sel-12 activity, we have conducted a clonal F2 screen of wild-type animals to identify mutations which mimic the "Bag of Dead Eggs" phenotype of the hop-1;sel-12 animals from hop-1/+;sel-12/+ mothers. We have screened 4800 genomes and have 8 potential suppressors. To determine if these mutations are involved in presenilin function, we are determining if the embryonic lethality is similar to the presenilin embryonic lethality. One may also test whether the mutations phenocopy presenilins in their interactions with lin-12(gf).

One may conduct a clonal F2 screen of lin-12(gf) animals to identify mutations which mimic the "Bag of Dead Eggs" phenotype, and which suppress lin-12(gf).

To identify targets involved in spe-4, hop-1 and sel-12 activity, one may conduct a clonal F2 screen for spermatogenesis-defective animals, which when mated into give a "Bag of Dead Eggs" phenotype.

To identify targets involved only in sel-12 activity, one may conduct a clonal F2 screen of hop-1 animals to identify mutations which mimic the "Bag of Dead Eggs" phenotype.

To identify targets involved only in hop-1 activity, one may conduct a clonal F2 screen of sel-12 animals to identify mutations which mimic the Glp Sterile phenotype.

Example 4

Nematode Mutagenesis

1. Mutagen Treatment.

Mutagenesis is performed on synchronous populations of L4 *C. elegans* larvae. Treatment of L4 animals is designed to maximize the exposure of germ cell precursors to mutagen treatment. A synchronous population of L4 animals is generated by either (i) treating a population of nematodes containing egg-bearing hermaphrodites with alkaline hypochlorite and placing the eggs (which survive the treatment) onto fresh Nematode Growth Medium plates seeded with *E. coli* for 52 hours at 20° C. or (ii) placing L1 onto fresh NGM plates seeded with *E. coli* for 48 hours at 20° C.

Treatment with potentially mutagenic chemicals is performed by dissolving or diluting the pure mutagen to the selected concentration in phosphate buffered saline and mixing the freshly, hatched L1 larvae (See e.g., Methods in Cell Biology, Volume 48, 1995 incorporated herein by reference (Eds. Epstein and Shakes, Academic Press, San Diego). The suspension of nematodes in mutagen is placed on a rocker table (to maintain mixing and aeration) for 3.5 to 4 hours at 20° C. The nematodes are then washed 3X with PBS and distributed to fresh seeded NGM plates. Progeny to the treated animals carry the newly induced mutations.

UV/TMP Variation:

Mutagenesis with ultraviolet radiation following treatment with trimethylpsoralen (TMP) is performed by first mixing L4 larvae with 0.3 mM TMP in PBS, 1% DMSO. After 15 minutes (in the dark) treated nematodes are transferred to an unseeded NGM plate in a small volume. After the liquid is absorbed (usually 5–10 minutes) the plates are irradiated with a calibrated UV lamp essentially as described by Yandall et al. (Proc. Natl. Acad. Sci., U.S.A., Vol. 91:1381–1385 (1994), incorporated herein by reference).

2. Monitoring mutagen treatment.

To monitor mutagenesis, one measures (i) the lethality of the potential mutagen to treated animals, (ii) the frequency at which their (F1) progeny fail to hatch from eggs and (iii) the frequency of ivermectin resistance among the F2 progeny. Determination of that fraction of single gene detectable deletions may be done using standard statistical techniques.

(i) Lethality of the mutagen to treated animals is determined by observing the treated animals by dissecting microscope 24 hours after exposure to mutagen treatment is completed. Animals that are dead, have failed to grow, or have no fertilized eggs within their gonads are judged to have been excessively affected by the mutagenesis.

(ii) The fraction of F1 eggs that fail hatch is determined by washing the mutagen treated animals off of the NGM plates, leaving unhatched eggs adhered to the agar surface. Afer 24 hours the plates are washed again and the number of hatched larvae and unhatched eggs are determined by counting.

(iii) Ivermectin is an anthelminthic drug used to control parasitic nematodes that infect livestock, pets and humans. Exposure of eggs of wild type *C. elegans* to NGM plates containing concentrations of ivermectin>2.5 microg/ml prevents the growth of *C. elegans* larvae. Selection of mutants that are resistant to the growth inhibiting effects of ivermectin provides a powerful screen for drug resistant mutants in *C. elegans*. Resistance to low levels of ivermectin (growth on 5–10 microg/ml of drug) is a phenotype conferred by single recessive mutations of more than 30 different genes. The frequency of low level ivermectin resistance thus acts as a convenient measure of the efficiency of mutagenesis leading to heritable genetic changes confined to single genes.

To measure the frequency of ivermectin resistance among populations of animals treated with a potential mutagen, we distribute 12 to 15 progeny (F1) of the mutagen treated animals per well into 96 wells of a first microtiter plate and, in a second plate, place 12 to 15 progeny of unmutagenized as a control. The nematodes are distributed as small larvae, suspended in liquid nematode growth medium seeded with *E. coli* as food. The microtiter plates are incubated at 20° C. until the larvae have grown to adults and produced several hundred eggs and about 100 larvae (F2 animals) per well, usually in about two days. (This number of progeny insures that all genomes will be represented in the F2's before F1's are exposed to ivermectin. The nematodes are not allowed to exhaust their food supply or to produce more than 200 larvae per well as the ivermectin resistance selection is less effective when a larger number of worms are present.

After two days, one counts the number of F1 adults in 24 wells of each plate. The mean, multiplied by 96, gives an estimate of the total number of F 1's in each plate. This value multiplied by two gives an estimate of the total number of genomes tested for resistance. The contents of each well are transferred to individual NGM plates seeded with *E. coli* and containing 7 ng/ml ivermectin. The plates are incubated at 20 to 23° C. and examined weekly for 4 weeks for the presence of viable, ivermectin resistant clones of animals. Those plates scored as resistant typically have several thousand worms growing on them including adults with eggs and these populations eventually completely consume the bacteria/food. Plates without resistant animals are generally devoid of viable animals; the original worms fail to grow and the culture eventually dies out. The number of plates that contain a resistant clone divided by the number of total number of genomes tested gives the ivermectin resistance frequency.

(iv) We have developed a strategy to measure the fraction of single gene mutations that are detectable deletions. This is important to optimize both mutagenesis and detection. The efficiency at which a mutagen treatment induce heritable genetic changes conferred to single genes (measured by the frequency of mutation to ivermectin resistance) multiplied by the fraction of single gene changes that result from detectable deletions provides the desired measure of the overall frequency at which the treatment generates detectable deletions.

The current approach involves identifying alleles of known genes and using PCR or Southern blotting to determine whether the alleles result from detectable deletions. Ivermectin resistance again provides a convenient tool for rapidly isolating alleles of known genes. Loss of function, including null, alleles in two genes, unc-33, and unc-44, confer both ivermectin resistance and a strong, highly characteristic, morphological and behavioral phenotype. We can isolate 25 to 50 unc-33 or unc-44 alleles for each mutagen treatment and determine with fraction of the alleles are conferred by detectable deletions.

3. Characteristics of an appropriate mutagen treatment.

The primary requirement of a mutagen treatment appropriate to use in the invention is that the mutagen generate a useable frequency of modest sized deletions (preferably between 0.5 and 3 kb). A useable frequency is defined as at least one mutation in 1,000,000 gemones screened. The most appropriate treatment will generate that highest frequency of detectable deletions. Other desirable characteristics include: (i) low toxicity to treated animals (i.e., less than 50%), and (ii) low level of killing of F1 eggs (i.e., less than 50%).

4. Appropriate mutagen treatments.

Table 4 lists five mutagens, which have proven effective based on the mutagen monitoring assays provided herein (see above). Libraries made with EMS, ENU, UV/TMP and DEO have all produced detectable deletions; DEB has not yet been used to make a library but we predict it will yield deletions.

Rejected Mutagens:

Formaldehyde, chlorambucil, acrylamide, diepoxyoyclooctane, hexamethylphosphoramide, and methylene-bis-acrylamide are specifically excluded from the methods of the invention. We have no evidence that these compounds produce single gene mutations based on results of the ivermectin resistance assay. We presume that these excluded mutagens are either not mutagenic in *C. elegans* under the conditions of the invention protocol, or that they produce larger, multigenic deletions or rearrangements which are not detected by our assay. Chlorambucil and particularly formaldehyde are also highly toxic to the treated worms. None of these compounds have been used to produce mutagenized libraries.

Example 5

Screen for deletions in Akt genes in *C. elegans*

The Akt gene encodes a serine-threonine protein kinase that is a critical mediator of growth factor-induced neuronal survival (Science 275:661–665, 1997). It has also been implicated to play a role in aspects of a number of other human diseases. We sought to knock out a homologue of the Akt gene located on cosmids R03El of *C. elegans* by screening for deletions using the polymerase chain reactions (PCR).

Figure 4:
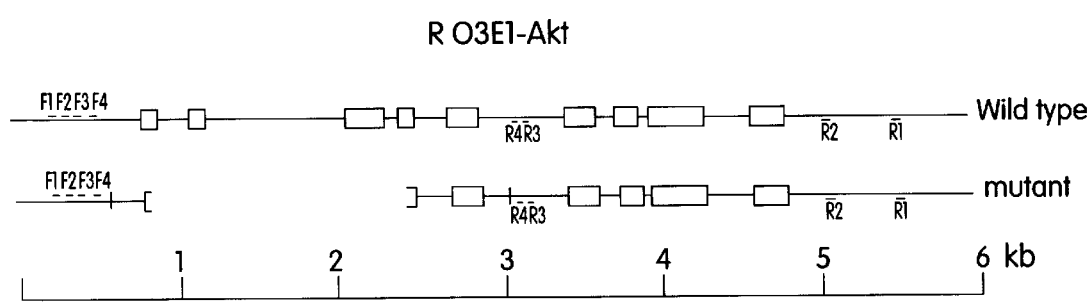
FIG. 4 shows a schematic representation of the wild type R03E1.akt gene and the identified deletion. Boxes represent predicted exons and lines between boxes represent introns. The approximate locations of the PCR primers used in the screens are indicated by horizontal short bars and primer names. The approximate location of the deletion is indicated by the gap. The two vertical short bars represent possible deletion end points.

Deletion screen in the Akt gene on R03E1:

Two set of primers (see Table 5, primer list), each comprising of two nested primer pairs, were chosen to screen mutagenized worm libraries by PCR for deletions in the Akt gene on R03E1. A total of 352,000 mutagenized genomes were screened in duplicate sets using the nested primers that were set approximately 3 kb apart. One potential deletion was identified from a UV-TMP mutagenized library. A second primer set was also used to screen the UV/TMP library. The second set of primers were placed approximately 5 kb apart and used to screen the UV/TMP library. One potential deletion was identified from the same pool (pool 36) from which the other deletion was found. These two deletion-containing bands are approximately 0.8 and 2.7 kb in length. The location of the primers (see Table 5 and FIG. 4) and the sizes of the deletion-containing bands suggest that the two independent screens using the two sets of primers identified the same deletion. Restriction mapping and sequencing may be performed to test this.

To confirm that the deletion bands represent true deletions, pool 36 was tested by PCR again for the presence of the deletion bands. Four independent PCR reactions were performed from each of the duplicate pool 36 using identical primers as in the initial screens. All but one PCR reactions tested positive for the presence of the deletion bands of the correct sizes. We therefore conclude that the deletion-containing bands represent a true deletion in the targeted gene.

The well that contains the deletion was identified by PCR using DNA from the 96-well microtiter plate that was used to make pool 36. DNA from each row and column of the plate was prepared and tested by PCR. Triplicate and duplicate PCR reactions were performed for each row and column, respectively. A PCR using DNA from one indicted well amplified a band of the expected length in all reactions. Thus, we conclude that that well contained the deletion.

TABLE I hop-1; sel-12 double mutant phenotypes.

| Maternal Genotype | Zygotic Genotype | Glp-like Defects | | Lin-12-like Defect |
| | | Sterile | Mel | 2AC†† |
|---|---|---|---|---|
| hop-1/+; sel-12* | hop-1; sel-12 | yes§ | N.A.¶ | 24/24 |
| hop-1; sel-12/+† | hop-1; sel-12 | no | yesII | 0/25 |
| hop-1/+; sel-12/+‡ | hop-1; sel-12 | no | yes** | N.D.‡‡ |

*The complete genotype is hop-1(nr2003)/unc-73(e936)dpy-5(e61); sel-12(nr2011).

†The complete genotype is either hop-1(nr2003); sel-12(nr2011)/pha-2(ad472)dpy-3(e27) or hop-1(nr2003); sel-12(nr2011)/egl-17(e1313)unc-1(e538).

‡The complete genotype is hop-1(nr2003)/unc-73(e936)dpy-5(e61); sel-12(nr2011)/+.

§non-Unc non-Dpy progeny (n = 147) of hop-1/unc-73 dpy-5; sel-12 mothers were cloned as L4s and incubated for 24–36 h. Of these, 60% were Egl and 40% were sterile. PCR analysis of 48 Egl and 44 sterile animals indicated that all of the Egl animals were heterozygous for the hop-1 deletion, whereas all of the sterile animals were hop-1 homozygotes. In a separate experiment, the germline phenotype of 59 young adult sterile animals was scored using DIC microscopy. Each gonad arm contained 50–100 sperm, no oocytes, and no undifferentiated germ cells (see FIG. 2), a phenotype resembling that of glp-1(lf) mutants (22).

¶N.A., not applicable

IInon-Dpy progeny (n = 287) of hop-1; sel-12/pha-2 dpy-3 mothers were cloned at the L4 and incubated for 24–36 h. Of these, 64% were wild type, 29% were filled with dead eggs (the Mel phenotype), 5% were Egl with live progeny and 2% were sterile. PCR analysis of 20 wild type and 20 Mel animals indicated that all of the wild type animals were heterozygous for the sel-12 deletion, whereas all of the Mel animals were sel-12 homozygotes. The Egl animals with live progeny were all sel-12 heterozygotes, indicating that in the absence of hop-1, a single wild-type copy of sel-12 is not always sufficient for normal egg laying. The rare sterile animals do not appear to have a germline proliferation defect; this sterility has not been characterized further.

TABLE I-continued

**Construction of the hop-1/+; sel-12 strain generated animals of the genotype hop-1/unc-73 dpy-5; sel-12/+ as intermediates. Twenty Egl, non-Unc non-Dpy progeny of these animals were cloned; fourteen segregated both Glp sterile and Unc Dpy animals (genotype hop-1/unc-73 dpy-5; sel-12), whereas six had a Mel phenotype, producing only dead embryos. The Mel animals were genotyped by PCR and all of them were hop-1; sel-12.

††The number of animals with two ACs and the total animals scored are indicated. Wild-type C. elegans hermaphrodite gonads generate a single anchor cell, whereas lin-12 null mutant gonads generate two (29). The number of ACs in non-Unc non-Dpy progeny of hop-1/unc-73 dpy-5; sel-12 mothers or non-Unc progeny of hop-1; sel-12/egl-17 unc-1 mothers was determined during L3 or L4 using DIC microscopy (see FIG. 2). After scoring, animals were allowed to develop to adulthood. Adult hop-1; sel-12 animals could be distinguished from their heterozygous siblings based on their sterile or Mel phenotype.

‡‡N.D., not determined.

TABLE 2

List of primers used to screen for sel-12 deletions

| Name | derives from | Sequence 5'–3' | pair with: | PCR product size |
|---|---|---|---|---|
| sel-12.F1 SEQ ID NO:7 | 1738–1758 | CATGTTCCATACTGGCAATCT | R1 | 3097 bp |
| sel-12.R1 SEQ ID NO:8 | 4835–4815 | TCCAGGTTTACTCCAGTCTTG | F1 | 3097 bp |
| sel-12.F2 SEQ ID NO:9 | 1913–1931 | GCTCAGGGTTGACACACTT | R2 | 2670 bp |
| sel-12.R2 SEQ ID NO:10 | 4583–4563 | TTACCTTTATTATTGGACGAA | F2 | 2670 bp |

TABLE 3

List of PCR primers used to screen for hop-1 deletions

| Name | derives from | Sequence 5'–3' | pair with: | PCR product size |
|---|---|---|---|---|
| hop-1.F1 SEQ ID NO:11 | 1991–2015 | TCAAAGACCGATAATGTTAGTTGTA | R1 | 2968 bp |
| hop-1.R1 SEQ ID NO:12 | 4958–4936 | TTCCAGATATGCCAACTGAAGTG | F1 | 2968 bp |
| hop-1.F2 SEQ ID NO:13 | 2098–2120 | GCCGACCTGAAAGATAATGAAAT | R2 | 2709 bp |
| hop-1.R2 SEQ ID NO:14 | 4806–4785 | ATAAAGCCGAAGGTTAGACGAT | F2 | 2709 bp |
| hop-1.F3 SEQ ID NO:15 | 2234–2256 | TTGTTTGAAAATAGGTGGTTTGG | R3 | 1574 bp |
| hop-1.R3 SEQ ID NO:16 | 3807–3787 | TCTGTCTGGGAATCACTGGAG | F3 | 1574 bp |

TABLE 4

| | Range | Preferred Range | % IVM$^T$ genomes |
|---|---|---|---|
| EMS (Ethyl methane sulfonate) | .05–2% | .25%–.5% | 1.2–2% |
| ENU (Ethyl nitroso urea) | 0.1–2.5 mM | .4–6 mM | 1–1.5% |
| UV*/TMP (Trimethylpsoralen) | 1500–20,000 uW × sec./cm$^2$ | 8,000–12,000 uW × sec./cm$^2$ | .5–.75% |
| DEO (Di-epoxyoctane) | 1–7.5 mM | 2–4 mM | .5–.8% |
| DEB (Di-epoxybutane) | .05–.5 mM | .05–.1 mM | .8–1.3% |

*UV dose is measured in microWatts per square centimeter times seconds of exposure.

TABLE 5

Akt
Primer List

| Name | derives from | Sequence 5'–3' | #nt | GC | Tm | pair with: | PCR |
|---|---|---|---|---|---|---|---|
| R03E1.F1 SEQ ID NO:17 | 8735–8756 | GCAGCAAAAAAGGTCACATCCC | 22 | 50 | 57 | R1 | 5285 |
| R03E1.R1 SEQ ID NO:18 | 14019–13996 | GTATGGCATGACAGATTTCCACAG | 24 | 46 | 55 | F1 | 5285 |
| R03E1.F2 SEQ ID NO:19 | 8752–8773 | ATCCCCTCTCTTCGCTGCTATC | 22 | 55 | 56 | R2 | 4842 |
| R03E1.R2 SEQ ID NO:20 | 13593–13570 | CAGGAAAGGAATGGAAATTAGCCC | 24 | 46 | 58 | F2 | 4842 |
| R03E1.F3 SEQ ID NO:21 | 8817–8839 | CCGCTCAAGTTTTGTCTGCAATC | 23 | 48 | 58 | R3 | 3075 |
| R03E1.R3 SEQ ID NO:22 | 11891–11869 | CGCCAGCATTATCACACTCTGTG | 23 | 52 | 57 | F3 | 3075 |
| R03E1.F4 SEQ ID NO:23 | 8879–8901 | CACTAGGGGTGTTTGTTTTTCCC | 23 | 48 | 56 | R4 | 2937 |
| R03E1.R4 SEQ ID NO:24 | 11815–11794 | AGAAAGGCGATGTTGTGAGGGC | 22 | 55 | 59 | F4 | 2937 |

What is claimed is:

1. A nematode having null mutations in hop-1 and sel-12, said nematode having a combined maternal-effect embryonic lethality and egg laying defective phenotype, at least one of said mutations being introduced by artifice, wherein said nematode is a *C. elegans* nematode.

* * * * *

UNITED STATES PATENT AND TRADEMARK OFFICE
CERTIFICATE OF CORRECTION

PATENT NO. : 6,278,039 B1
DATED : August 21, 2001
INVENTOR(S) : Johnson et al.

It is certified that error appears in the above-identified patent and that said Letters Patent is hereby corrected as shown below:

Column 1,
Line 14, change "AD extracellular" to -- AD are extracellular --; and
Line 29, change "APP First" to -- APP. First --.

Column 2,
Line 21, change "number viable" to -- number of viable --; and
Line 47, change "offspring," to -- offspring --.

Column 3,
Line 53, change "capable encoding" to -- capable of encoding --.

Column 4,
Line 36, change "os" to -- of --;
Line 42, change "embryof" to -- embryos --; and
Line 67, change "wight" to -- weight --.

Column 5,
Line 15, change "nr201 I-mutants" to -- nr2011 mutants --.

Column 6,
Line 16, change "150C" to -- 15 C --.

Column 7,
Line 5, change "respond" to -- respond to --;
Line 12, change "maternally-10 contributed" to -- maternally-contributed --; and
Line 37, change "gap-1" to -- glp-1 --.

Column 9,
Line 42, change "are both" to -- both --; and
Line 47, change "thus be" to -- thus --.

Column 10,
Line 3, change "knockouts such" to -- knockouts. Such --;
Line 46, change "phenocoping" to -- phenocopying --;
Line 48, change "then" to -- than --;
Line 54, change "is less" to -- is a less --;
Line 56, change "addition, identify" to -- addition, can identify --; and
Line 66, change "Presenline" to -- Presenilin --.

UNITED STATES PATENT AND TRADEMARK OFFICE
CERTIFICATE OF CORRECTION

PATENT NO.    : 6,278,039 B1
DATED         : August 21, 2001
INVENTOR(S)   : Johnson et al.

It is certified that error appears in the above-identified patent and that said Letters Patent is hereby corrected as shown below:

Column 11,
Line 45, change "approaches" to -- approaches. --.

Column 12,
Line 58, change "1974)." to -- 1974) --; and
Line 67, change "(e27)" to -- (e27). --.

Column 13,
Line 7, change "modem" to -- modern --.

Column 14,
Line 64, change "HB11" to -- HB101 --.

Column 15,
Line 38, change "worms" to -- worm --.

Column 16,
Line 15, change "form" to -- from --; and
Line 40, change "simi-dominantly" to -- semi-dominantly --.

Column 17,
Line 48, change "fail hatch" to -- fail to hatch --.

Column 18,
Line 5, change "unmutagenized" to -- unmutagenized animals --;
Line 31, delete "number of";
Line 37, change "induce" to -- induces --;
Line 53, change "with" to -- which --; and
Line 60, change "gemones" to -- genomes --.

UNITED STATES PATENT AND TRADEMARK OFFICE
CERTIFICATE OF CORRECTION

PATENT NO.   : 6,278,039 B1
DATED        : August 21, 2001
INVENTOR(S)  : Johnson et al.

It is certified that error appears in the above-identified patent and that said Letters Patent is hereby corrected as shown below:

Column 19,
Line 31, delete "of".

Column 20,
Line 20, change "reactions" to -- reaction --.

Signed and Sealed this

Twenty-fourth Day of August, 2004

JON W. DUDAS
*Director of the United States Patent and Trademark Office*